US012559539B2

(12) United States Patent
Tian et al.

(10) Patent No.: US 12,559,539 B2
(45) Date of Patent: Feb. 24, 2026

(54) TGF-BETA RECEPTOR FUSION PROTEIN PHARMACEUTICAL COMPOSITION AND USE THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Chenmin Tian, Shanghai (CN); Hao Li, Shanghai (CN); Xun Liu, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1128 days.

(21) Appl. No.: 17/290,707

(22) PCT Filed: Nov. 8, 2019

(86) PCT No.: PCT/CN2019/116593
§ 371 (c)(1),
(2) Date: Apr. 30, 2021

(87) PCT Pub. No.: WO2020/094122
PCT Pub. Date: May 14, 2020

(65) Prior Publication Data
US 2022/0017601 A1     Jan. 20, 2022

(30) Foreign Application Priority Data

Nov. 9, 2018     (CN) .......................... 201811328326.1

(51) Int. Cl.
| | |
|---|---|
| *C07K 14/71* | (2006.01) |
| *A61K 38/00* | (2006.01) |
| *A61K 39/00* | (2006.01) |
| *A61K 47/68* | (2017.01) |
| *A61P 35/00* | (2006.01) |
| *C07K 16/28* | (2006.01) |

(52) U.S. Cl.
CPC .......... *C07K 14/71* (2013.01); *A61K 47/6849* (2017.08); *A61P 35/00* (2018.01); *C07K*
*16/2827* (2013.01); *A61K 38/00* (2013.01); *A61K 2039/505* (2013.01)

(58) Field of Classification Search
None
See application file for complete search history.

(56) References Cited

FOREIGN PATENT DOCUMENTS

| | | | | |
|---|---|---|---|---|
| CN | 101397343 A | 4/2009 | | |
| WO | 9309228 A1 | 5/1993 | | |
| WO | 9409815 A1 | 5/1994 | | |
| WO | 2006074451 A2 | 7/2006 | | |
| WO | 2009152610 A1 | 12/2009 | | |
| WO | 2011109789 A2 | 9/2011 | | |
| WO | 2013164694 A1 | 11/2013 | | |
| WO | 2014164427 A1 | 10/2014 | | |
| WO | 2015077540 A2 | 5/2015 | | |
| WO | 2015118175 A2 | 8/2015 | | |
| WO | 2015183943 A2 | 12/2015 | | |
| WO | WO-2017084495 A1 * | 5/2017 | .......... | A61K 39/395 |
| WO | WO-2018129331 A1 * | 7/2018 | ................ | A61J 1/10 |
| WO | 2018205985 A1 | 11/2018 | | |

OTHER PUBLICATIONS

Jonghwa Won et al, Tumorigenicity of Mouse Thymoma Is Suppressed by Soluble Type II Transforming Growth Factor β Receptor Therapy, Cancer Research, Mar. 15, 1999, vol. 59, pp. 1273-1277.
Yan Lan et al, Enhanced Preclinical Antitumor Activity of M7824, a Bifunctional Fusion Protein Simultaneously Targeting PD-L1 and TGF-β, Science Translational Medicine, Jan. 17, 2018, vol. 10, No. 424.

* cited by examiner

*Primary Examiner* — James H Alstrum-Acevedo
*Assistant Examiner* — Tara L Martinez
(74) *Attorney, Agent, or Firm* — Morgan, Lewis & Bockius LLP

(57) ABSTRACT

Disclosed in the present disclosure are a TGF-β receptor fusion protein pharmaceutical composition and a use thereof. Specifically, the pharmaceutical composition comprises a TGF-β receptor fusion protein in a sodium citrate buffer, and the TGF-β receptor fusion protein comprises a PD-L1 antibody targeting portion and a TGF-βRII extracellular region. In addition, the pharmaceutical composition may also comprise a sugar and a non-ionic surfactant.

14 Claims, 6 Drawing Sheets

Specification includes a Sequence Listing.

Truncated TGF-βRII extracellular region

TGF-BETA RECEPTOR FUSION PROTEIN PHARMACEUTICAL COMPOSITION AND USE THEREOF

CROSS-REFERENCE TO RELATED APPLICATIONS

The present application is the national stage of International Patent Application No. PCT/CN2019/116593, filed Nov. 8, 2019, which claims the benefit of and priority to Chinese Patent Application No. 201811328326.1, filed on Nov. 9, 2018, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 23, 2025, is named "719079CPCT_seqlisting_Revised.TXT" and is 44,209 bytes in size.

FIELD OF THE INVENTION

The present disclosure belongs to the field of pharmaceutical preparation, and in particular relates to a pharmaceutical composition comprising PD-L1 antibody/TGF-βRII extracellular region fusion protein, and the use thereof as a medicament.

BACKGROUND OF THE INVENTION

The statements herein only provide background information related to the present disclosure, and do not necessarily constitute the prior art.

During tumor treatment, people have recognized the high toxicity due to chemotherapy, and chemotherapy can lead to the generation of drug-resistant cancer cells. Even if targeted therapies are used, which target over-expressed or over-activated proteins related to tumor survival and growth, there will still be cancer cells that are mutated to reduce or evade the dependence on pathways targeted by the targeted therapy, and those cancer cells would survive via other pathways.

Tumor immunotherapy has attracted much attention in recent years, and is the focus in the field of tumor treatment. The outstanding advantage of such therapy is the increased difficulty in generating drug resistance. Tumor immunotherapy mainly uses immunological principles and methods to improve the immunogenicity of tumor cells and the sensitivity to effector cell killing, and to stimulate and enhance the anti-tumor immune response in organism. Tumor immunotherapy involves the infusion of immune cells and effector molecules into a host, and these two cooperate with the immune system to kill tumors and inhibit tumor growth in organism.

Programmed death receptor 1 (PD-1) is a member of the CD28 superfamily. PD-1 is expressed on activated T cells, B cells and myeloid cells. PD-1 has two ligands, programmed death ligand 1 (PD-L1) and PD-L2. PD-L1 interacts with the receptor PD-1 on T cells, and plays an important role in the negative regulation of immune response. The expression of PD-L1 protein can be detected in many human tumor tissues. The microenvironment at the tumor site can induce the expression of PD-L1 on tumor cells, and the expressed PD-L1 in turn contributes to the tumorigenesis and growth, and induces the apoptosis of anti-tumor T cells. The inhibitors of PD-1/PD-L1 pathway block the binding of PD-1 to PD-L1, block negative regulatory signals, restore T cell activity, and enhance immune response. Therefore, immunomodulation with PD-1/PD-L1 as the target is of great significance to tumor suppression.

Transforming growth factor-β (TGF-β) belongs to the TGF-β superfamily that regulates cell growth and differentiation. TGF-β transmits signals through a heterotetrameric receptor complex, which is composed of two type I and two type II transmembrane serine/threonine kinase receptors.

TGF-β is a multifunctional cytokine, which exerts a tumor-suppressing or tumor-promoting effect in a cell-dependent or background-dependent manner. The tumor-suppressing effect of TGF-β depends on the ability to induce the expression of multiple genes. When mutations or epigenetic modifications are introduced during tumor development, cancer cells are gradually tolerant to the inhibitory effect of TGF-β, which ultimately leads to tumor development.

Studies have found that blocking the TGF-β signaling pathway can reduce tumor metastasis. It was found that the metastasis ability of tumor cells was inhibited when the TGF-β signaling pathway of breast tumor cell lines was inhibited by the truncated Smad2/3 negative mutant. The study of the instability of colon cancer microsatellite found that the inactive mutation of TGF-βRII reduced metastasis and increased the postoperative survival rate of patients. However, in general, the effect is weak when inhibitor of TGF-β signaling pathway is administered alone in clinical treatment, probably because TGF-β is mainly abnormally expressed in tumor cells, whereas it is difficult for the inhibitor of TGF-β signaling pathway alone to target tumor, resulting in low efficacy or low bioavailability of the inhibitor.

Therefore, on the basis of targeting and neutralizing TGF-β in a tumor microenvironment, inhibiting the PD-1/PD-L1 pathway can restore the activity of T cells, enhance the immune response, and improve the inhibiting effect of tumorigenesis and development more effectively.

A previous PCT application of the applicant PCT/CN2016/104320 (publication number WO2017084495) provides a PD-L1 antibody. Antibody/TGF-β receptor fusion protein has been published at present, such as in WO2006074451A2, WO2009152610A1, WO2011109789A2, WO2013164694A1, WO2014164427A1, WO2015077540A2, WO9309228A1, WO9409815A1, WO2015077540A2, WO2015118175A2, etc. Among them, Merck discloses a PD-L1/TGF-β bifunctional fusion protein Bintrafusp Alfa (WO2015118175, also known as M7824, FP17022). Currently, Bintrafusp Alfa has been in clinical phase of tumor diseases such as gastric cancer, lung cancer, esophageal cancer, NSCLC, biliary cancer. However, the antibody medicaments in the prior art become unstable due to large molecular weights, complex structures, and being susceptible to degradation, polymerization or occurrence of undesirable chemical modifications. In order to make the antibody suitable for administration, maintain stability during storage and subsequent use, and to exert a better effect, the research on stable preparations of antibody medicaments is particularly important.

SUMMARY OF THE INVENTION

The present disclosure provides a pharmaceutical composition comprising a PD-L1/TGF-βRII fusion protein, which is more conducive to production and administration, and is more stable in performance: the pharmaceutical composition comprises:

a TGF-β receptor fusion protein, and a buffer, wherein the buffer is selected from the group consisting of a histidine salt buffer, a succinate buffer, a phosphate buffer and a citrate buffer.

In some embodiments, the buffer is a citrate buffer. In some embodiments, the histidine salt buffer is histidine-hydrochloric acid buffer; and the succinate buffer is succinic acid-sodium succinate buffer: the citrate buffer is citric acid-sodium citrate buffer: In some embodiments, the buffer is citric acid-citrate sodium buffer.

In an alternative embodiment, the concentration of the TGF-β receptor fusion protein in the pharmaceutical composition described above is about 0.5 mg/ml to about 100 mg/ml, preferably about 30 mg/ml to about 70 mg/ml.

In some embodiments, the concentration of the TGF-β receptor fusion protein in the pharmaceutical composition is 0.5 mg/ml to 100 mg/ml, preferably 30 mg/ml to 70 mg/ml. The non-limiting examples of the concentration of TGF-β receptor fusion protein involve: about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, preferably about 50 mg/ml.

In some embodiments, the concentration of the TGF-β receptor fusion protein in the pharmaceutical composition is 30 mg/ml, 35 mg/ml, 40 mg/ml, 45 mg/ml, 50 mg/ml, 55 mg/ml, 60 mg/ml, 65 mg/ml, 70 mg/ml, more preferably 50 mg/ml.

In an alternative embodiment, the pH value of the buffer in the pharmaceutical composition described above is about 5.0 to about 7.5, preferably about 6.0 to about 6.5, and optionally about 6.0, about 6.1, about 6.2, about 6.3, about 6.4, about 6.5, more preferably about 6.2.

In some embodiments, the pH value of the buffer is 5.0 to 7.5, or 6.0 to 6.5, preferably 6.0, 6.1, 6.2, 6.3, 6.4 or 6.5, more preferably 6.2.

In an alternative embodiment, the concentration of the buffer is about 5 mM to about 30 mM, preferably about 5 mM to about 20 mM; non-limiting examples thereof involve 5 mM, 6 mM, 7 mM, 8 mM, 9 mM, 10 mM, 12 mM, 14 mM, 16 mM, 18 mM, 20 mM, more preferably 10 mM.

In some embodiments, the concentration of the buffer is 5 mM to 30 mM, preferably 5 mM to 20 mM; and in some embodiments, the concentration of the buffer is about 10 mM, about 12 mM, about 14 mM, about 16 mM, about 18 mM, about 20 mM, and more preferably about 10 mM.

In an alternative embodiment, the pharmaceutical composition described above also comprises saccharide. The "saccharide" in the present disclosure comprises conventional compounds/compositions $(CH_2O)_n$ or derivatives thereof, comprising monosaccharides, disaccharides, trisaccharides, polysaccharides, sugar alcohols, reducing saccharides, non-reducing saccharides, and the like. In some embodiments, the saccharide is selected from the group consisting of: glucose, sucrose, trehalose, lactose, fructose, dextran, glycerol, erythritol, glycerol, arabitol, xylitol, sorbitol, mannitol, melibiose, melezitose, melitriose, mannotriose, stachyose, maltose, lactulose, maltulose, sorbitol, malitol, lactitol, iso-maltulose and so on. The preferred saccharide is a non-reducing disaccharide, more preferably trehalose or sucrose, and most preferably sucrose.

In an alternative embodiment, the concentration of the saccharide in the pharmaceutical composition described above is about 50 mg/ml to about 100 mg/ml, preferably about 60 mg/ml to about 90 mg/ml; non-limiting examples involve 60 mg/ml, 65 mg/ml, 70 mg/ml, 75 mg/ml, 80 mg/ml, 85 mg/ml, 90 mg/ml, most preferably 80 mg/ml.

In some embodiments, the concentration of the saccharide is 50 mg/ml to 100 mg/ml, preferably 60 mg/ml to 90 mg/ml; and in some embodiments, the concentration of the saccharide is about 60 mg/ml, about 65 mg/ml, about 70 mg/ml, about 75 mg/ml, about 80 mg/ml, about 85 mg/ml or about 90 mg/ml.

In an alternative embodiment, the pharmaceutical composition described above further comprises a surfactant, which may be selected from the group consisting of polysorbate 20, polysorbate 80, polyhydroxyalkylene, Triton, sodium dodecyl sulfonate, sodium lauryl sulfonate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, laurel amidopropyl-betaine, cocaamidopropyl-betaine, linoleamidopropyl-betaine, myristamidopropyl-betaine, palmitamidopropyl-betaine, isostearyl amidopropyl-betaine, myristamidopropyl-dimethylamine, palmamidopropyl-dimethylamine, isostearamidopropyl-dimethylamine, sodium methyl cocoyl, sodium methyl oleyl taurate, polyethylene glycol, polypropylene glycol, copolymer of ethylene and propylene glycol, etc. The preferred surfactant is polysorbate 80 or polysorbate 20, more preferably polysorbate 80.

In another alternative embodiment, the concentration of the surfactant in the pharmaceutical composition described above is about 0.1 mg/ml to about 0.8 mg/ml, more preferably about 0.4 mg/ml to about 0.8 mg/ml. In some embodiments, the concentration of the surfactant is 0.1 mg/ml to 0.8 mg/ml, preferably 0.4 mg/ml to 0.8 mg/ml, more preferably about 0.4 mg/ml, about 0.45 mg/ml, about 0.5 mg/ml, about 0.55 mg/ml, about 0.6 mg/ml, about 0.7 mg/ml, about 0.8 mg/ml.

In some embodiments, the concentration of the surfactant is 0.4 mg/ml, 0.45 mg/ml, 0.5 mg/ml, 0.55 mg/ml, 0.6 mg/ml, 0.7 mg/ml or 0.8 mg/ml, more specifically 0.4 mg/ml.

In an alternative embodiment, the pharmaceutical composition described above comprises: (a) about 0.5 mg/ml to about 100 mg/ml TGF-β receptor fusion protein, (b) about 5 mM to about 30 mM citrate buffer, (c) about 50 mg/ml to about 100 mg/ml sucrose, and (d) about 0.1 mg/ml to about 0.8 mg/ml polysorbate 80, preferably the pH of the pharmaceutical composition is about 5.0 to about 7.5, more preferably about 6.0 to about 6.5.

In an alternative embodiment, the pharmaceutical composition described above comprises:

| | |
|---|---|
| 0.5 mg/ml to 100 mg/ml | TGF-β receptor fusion protein |
| 5 mM to 30 mM | citrate buffer |
| 50 mg/ml to 100 mg/ml | sucrose, and |
| 0.1 mg/ml to 0.8 mg/ml | polysorbate 80; | preferably, the pH of the pharmaceutical composition is 5.0 to 7.5, more preferably 6.0 to 6.5.

In an alternative embodiment, the pharmaceutical composition described above comprises: (a) about 30 mg/ml to about 70 mg/ml TGF-β receptor fusion protein, (b) about 5 mM to about 20 mM citric acid-sodium citrate buffer, (c) about 60 mg/ml to about 90 mg/ml sucrose, and (d) about 0.4 mg/ml to about 0.8 mg/ml polysorbate 80, preferably, the pH of the pharmaceutical composition is about 6.0 to about 6.5.

In an alternative embodiment, the pharmaceutical composition described above comprises:

| | |
|---|---|
| 30 mg/ml to 70 mg/ml | TGF-β receptor fusion protein |
| 5 mM to 20 mM | citric acid-sodium citrate buffer |
| 60 mg/ml to 90 mg/ml | sucrose, and |
| 0.4 mg/ml to 0.8 mg/ml | polysorbate 80; | the pH of the pharmaceutical composition is about 6.0 to about 6.5.

In an alternative embodiment, the pharmaceutical composition comprises: (a) about 50 mg/ml TGF-β receptor fusion protein, (b) about 10 mM citric acid-sodium citrate buffer, (c) about 80 mg/ml sucrose, and (d) about 0.4 mg/ml polysorbate 80, the pH of the pharmaceutical composition is preferably about 6.2.

In an alternative embodiment, the pharmaceutical composition comprises:

| | |
|---|---|
| 50 mg/ml | TGF-β receptor fusion protein |
| 10 mM | citric acid-sodium citrate buffer |
| 80 mg/ml | sucrose, and |
| 0.4 mg/ml | polysorbate 80; | preferably, the pH of the pharmaceutical composition is about 6.2.

In an alternative embodiment, the TGF-β receptor fusion protein in the pharmaceutical composition described above is shown as general formula (I):

$$Ab-L-TGF-\beta RII\ ECD \qquad\qquad (I)$$

wherein, the TGF-βRII ECD is a truncated form of an extracellular region of TGF-βRII;

Ab is a PD-L1 antibody or antigen-binding fragment thereof;

L is a linker sequence.

In an alternative embodiment, the linker sequence in the pharmaceutical composition described above is $(G_4S)_xG$, wherein x is an integer of 3-6. In an alternative embodiment, x is 3, 4, 5 or 6, preferably 4. In an alternative embodiment, the linker sequence in the pharmaceutical composition described above is GGGGSGGGGSGGGGSG (SEQ ID NO: 25), GGGGSGGGGSGGGGSGGGGSG (SEQ ID NO: 26), GGGGSGGGGSGGGGSGGGGSGGGGSG (SEQ ID NO: 27 or GGGGSGGGGSGGGGSGGGGSGGGGSGGGGSG (SEQ ID NO: 28).

In an alternative embodiment, the truncated form of the extracellular region of TGF-βRII is a sequence of TGF-βRII extracellular domain (shown as SEQ ID NO: 14) with a deletion of at most 26 consecutive amino acid residues at amino terminus (also referred as N terminus). In some embodiments, the truncated form of the extracellular region of TGF-βRII is a sequence of TGF-βRII extracellular domain with a deletion of 14, 15, 16, 17, 18, 19, 20, 21, 22, 23, 24, 25 or 26 consecutive amino acid residues at N terminus. In some embodiments, the sequence of the TGF-βRII ECD in the pharmaceutical composition described above is shown as SEQ ID NO: 14, 15, 16 or 17; preferably, the sequence shown as SEQ ID NO: 15.

In an alternative embodiment, the PD-L1 antibody or antigen-binding fragment thereof in the pharmaceutical composition described above comprises:

HCDR1, HCDR2 and HCDR3 shown as SEQ ID NO: 1, SEQ ID NO: 2 and SEQ ID NO: 3, respectively; and

LCDR1, LCDR2 and LCDR3 shown as SEQ ID NO: 4, SEQ ID NO: 5 and SEQ ID NO: 6, respectively.

In an alternative embodiment, the PD-L1 antibody or antigen-binding fragment thereof in the pharmaceutical composition described above comprises:

HCDR1, HCDR2 and HCDR3 shown as SEQ ID NO: 1, SEQ ID NO: 10 and SEQ ID NO: 3, respectively, and LCDR1, LCDR2 and LCDR3 shown as SEQ ID NO: 4, SEQ ID NO: 5 and SEQ ID NO: 6, respectively.

In an alternative embodiment, the PD-L1 antibody or antigen-binding fragment thereof in the pharmaceutical composition described above comprises:

a heavy chain variable region shown as SEQ ID NO: 7 and a light chain variable region shown as SEQ ID NO: 8:

or, comprises:

a heavy chain variable region shown as SEQ ID NO: 9 and a light chain variable region shown as SEQ ID NO: 11.

In an alternative embodiment, the heavy chain amino acid sequence of the PD-L1 antibody in the pharmaceutical composition described above is shown as SEQ ID NO: 12 or has at least 85%, 86%, 87%, 88%, 89%, 90%, 91%, 92%, 93%, 94%, 95%, 96%, 97%, 98%, 99% or 100% sequence identity to the amino acid sequence shown as SEQ ID NO: 12: the light chain amino acid sequence of the PD-L1 antibody is shown as SEQ ID NO: 13 or has at least 85%, 86%, 87%, 88%, 89%, 90%, 91%, 92%, 93%, 94%, 95%, 96%, 97%, 98%, 99% or 100% sequence identity to the amino acid sequence shown as SEQ ID NO: 13.

In an alternative embodiment of the pharmaceutical composition described above, in the TGF-β receptor fusion protein, the TGF-βRII ECD is fused to the carboxyl terminus of the PD-L1 antibody heavy chain through a linker sequence.

In some embodiments, the TGF-β receptor fusion protein comprises:

a fusion peptide formed by the heavy chain of the PD-L1 antibody fused to TGF-βRII ECD, the sequence of which is shown as SEQ ID NO: 23 or has at least 85%, 86%, 87%, 88%, 89%, 90%, 91%, 92%, 93%, 94%, 95%, 96%, 97%, 98%, 99% or 100% sequence identity to the sequence shown as SEQ ID NO: 23, and the light chain of the PD-L1 antibody, the sequence of which is shown as SEQ ID NO: 13 or has at least 85%, 86%, 87%, 88%, 89%, 90%, 91%, 92%, 93%, 94%, 95%, 96%, 97%, 98%, 99% or 100% sequence identity to the sequence shown as SEQ ID NO: 13.

In other embodiments, the TGF-β receptor fusion protein comprises:

a fusion peptide formed by the heavy chain of the PD-L1 antibody fused to TGF-βRII ECD, the sequence of which is shown as SEQ ID NO: 24 or has at least 85%, 86%, 87%, 88%, 89%, 90%, 91%, 92%, 93%, 94%, 95%, 96%, 97%, 98%, 99% or 100% sequence identity to the sequence shown as SEQ ID NO: 24, and the light chain of the PD-L1 antibody, the sequence of which is shown as SEQ ID NO: 13 or has at least 85%, 86%, 87%, 88%, 89%, 90%, 91%, 92%, 93%, 94%, 95%, 96%, 97%, 98%, 99% or 100% sequence identity to the sequence shown as SEQ ID NO: 13.

The present disclosure also provides a method for preparing the pharmaceutical composition described above, which comprises a step of contacting TGF-β receptor fusion protein with a buffer, for example, performing buffer replacement on the TGF-β receptor fusion protein stock solution, and the buffer is preferably citrate buffer; more preferably citric acid-sodium citrate buffer, the concentration of the buffer is preferably about 5 mM to about 20 mM: the non-limiting examples involve 5 mM, 6 mM, 7 mM, 8 mM, 9 mM, 10 mM, 12 mM, 14 mM, 16 mM, 18 mM, 20 mM, more preferably 10 mM: the pH of the buffer is about 6.0 to about 6.5, the non-limiting examples involve 6.0, 6.1, 6.2, 6.3, 6.4, 6.5, preferably 6.2. In an alternative embodiment, the concentration of the buffer is 5 mM to 20 mM, the non-limiting examples involve about 5 mM, about 6 mM, about 7 mM, about 8 mM, about 9 mM, about 10 mM, about 12 mM, about 14 mM, about 16 mM, about 18 mM, about 20 mM, more preferably about 10 mM; the pH of the buffer is 6.0 to 6.5, the non-limiting examples involve about 6.0, about 6.1, about 6.2, about 6.3, about 6.4, about 6.5, preferably about 6.2.

The present disclosure also provides a method for preparing the pharmaceutical composition described above, further comprising the following steps after contacting the TGF-β receptor fusion protein with the buffer: adding sucrose and polysorbate 80 to the obtained solution (no precedence order between the two), and then adjusting the volume with the buffer, wherein the concentration of the buffer solution is preferably about 5 mM to about 20 mM, more preferably 5 mM to 20 mM, the non-limiting examples involve 5 mM, 8 mM, 10 mM, 12 mM, 14 mM, 16 mM, 18 mM, 20 mM: the pH of the buffer is about 6.0 to about 6.5, the non-limiting examples involve 6.0, 6.1, 6.2, 6.3, 6.4, 6.5.

The present disclosure also provides a method for preparing a lyophilized preparation comprising TGF-β receptor fusion protein, which comprises a step of lyophilizing the pharmaceutical composition described above.

In an alternative embodiment, the method for preparing a lyophilized preparation described above comprising the TGF-β receptor fusion protein, wherein the lyophilization is performed according to a method known in the art, such as but not limited to steps comprising pre-freezing, primary drying and secondary drying. The skilled persons understand that any method for removing water from the pharmaceutical composition in the present disclosure is applicable to the present disclosure.

The present disclosure also provides a lyophilized preparation comprising the TGF-β receptor fusion protein, which is prepared by the method for preparing a lyophilized preparation described above.

The present disclosure also provides a lyophilized preparation comprising the TGF-β receptor fusion protein, which can be reconstituted to form the pharmaceutical composition described above.

In some embodiments, the lyophilized preparation can be stable at 2° C. to 8° C. for at least 3 months, at least 6 months, at least 12 months, at least 18 months, or at least 24 months. In some embodiments, the lyophilized preparation can be stable at 40° C. for at least 7 days, at least 14 days, or at least 28 days.

The present disclosure also provides a reconstituted solution comprising the TGF-β receptor fusion protein, which is obtained by re-reconstituting the lyophilized preparation comprising TGF-β receptor fusion protein described above.

The present disclosure also provides a method for preparing the reconstituted solution comprising the TGF-β receptor fusion protein described above, which comprises: a step of re-reconstituting the lyophilized preparation described above, the solution used for reconstitution comprises, but is not limited to, water for injection, physiological saline or glucose solution, preferably water for injection.

The present disclosure further provides an article of manufacture or kit, comprising: the pharmaceutical composition according to the present disclosure; and container(s).

In some embodiments, the container is a glass bottle, such as but not limited to, an injection bottle made of neutral borosilicate glass vial.

The present disclosure also provides an article of manufacture, comprising container(s), which comprise(s) the pharmaceutical composition described above, or the lyophilized preparation thereof, or a reconstituted solution of the lyophilized preparation.

The present disclosure also provides the use of any one selected from the following in the preparation of a medicament:

the pharmaceutical composition described above, or the lyophilized preparation, or the reconstituted solution of the lyophilized preparation, or the article of manufacture; the medicament is used to treat or inhibit disease(s) or disorder(s) of tumor cell proliferation or metastasis.

In some embodiments, the disease(s) or disorder(s) is/are tumor.

In some embodiments, the disease(s) or disorder(s) is/are selected from the group consisting of: colorectal cancer, breast cancer, ovarian cancer, pancreatic cancer, gastric cancer, prostate cancer, kidney cancer, cervical cancer, myeloma, lymphoma, leukemia, thyroid cancer, endometrial cancer, uterine cancer, bladder cancer, neuroendocrine cancer, head and neck cancer, liver cancer, nasopharyngeal carcinoma, testicular cancer, lung cancer, small cell lung cancer, non-small cell lung cancer, melanoma, basal cell cutaneous carcinoma, squamous cell cutaneous carcinoma, dermatofibrosarcoma protuberans, Merkel cell carcinoma, glioblastoma, glioma, sarcoma, mesothelioma, and myelodysplastic syndrome.

The present disclosure also provides a method for treating or inhibiting disease(s) or disorder(s) related to proliferation or metastasis of cancer cell, comprising providing a therapeutically effective amount of the pharmaceutical composition described above or the lyophilized preparation, or the reconstituted solution, or the article of manufacture, to a subject in need. In some embodiments, the method comprises administering to the subject a unit dose of composition comprising: 0.1 mg to 3000 mg of the TGF-β receptor fusion protein as described above, the pharmaceutical composition, or the lyophilized preparation, or the reconstituted solution, or the article of manufacture. In some embodiments, the disease(s) or disorder(s) is/are tumor. In some embodiments, the disease(s) or disorder(s) is/are selected from the group consisting of: colorectal cancer, breast cancer, ovarian cancer, pancreatic cancer, gastric cancer, prostate cancer, kidney cancer, cervical cancer, myeloma, lymphoma, leukemia, thyroid cancer, endometrial cancer, uterine cancer, bladder cancer, neuroendocrine cancer, head and neck cancer, liver cancer, nasopharyngeal carcinoma, testicular cancer, lung cancer, small cell lung cancer, non-small cell lung cancer, melanoma, basal cell cutaneous carcinoma, squamous cell cutaneous carcinoma, dermatofibrosarcoma protuberans, Merkel cell carcinoma, glioblastoma, glioma, sarcoma, mesothelioma, and myelodysplastic syndrome.

The present invention also provides the TGF-β receptor fusion protein, pharmaceutical composition, or lyophilized preparation, or reconstituted solution, or article of manufacture described above, for treating or inhibiting disease(s) or disorder(s) related to proliferation or metastasis of cancer cell. In some embodiments, the disease(s) or disorder(s) is/are tumor. In some embodiments, the disease(s) or disorder(s) is/are selected from the group consisting of: colorectal cancer, breast cancer, ovarian cancer, pancreatic cancer, gastric cancer, prostate cancer, kidney cancer, cervical cancer, myeloma, lymphoma, leukemia, thyroid cancer, endometrial cancer, uterine cancer, bladder cancer, neuroendocrine cancer, head and neck cancer, liver cancer, nasopharyngeal carcinoma, testicular cancer, lung cancer, small cell lung cancer, non-small cell lung cancer, melanoma, basal cell cutaneous carcinoma, squamous cell cutaneous carcinoma, dermatofibrosarcoma protuberans, Merkel cell carcinoma, glioblastoma, glioma, sarcoma, mesothelioma, and myelodysplastic syndrome.

As is well known to those skilled in the art, one, some or all of the features of the various embodiments described in the present disclosure can be further combined to form other embodiments of the present disclosure. The above embodiments of the present disclosure and other embodiments obtained by combination are further illustrated by the following detailed description.

DETAILED DESCRIPTION OF THE INVENTION

Terminology

Figure 1:
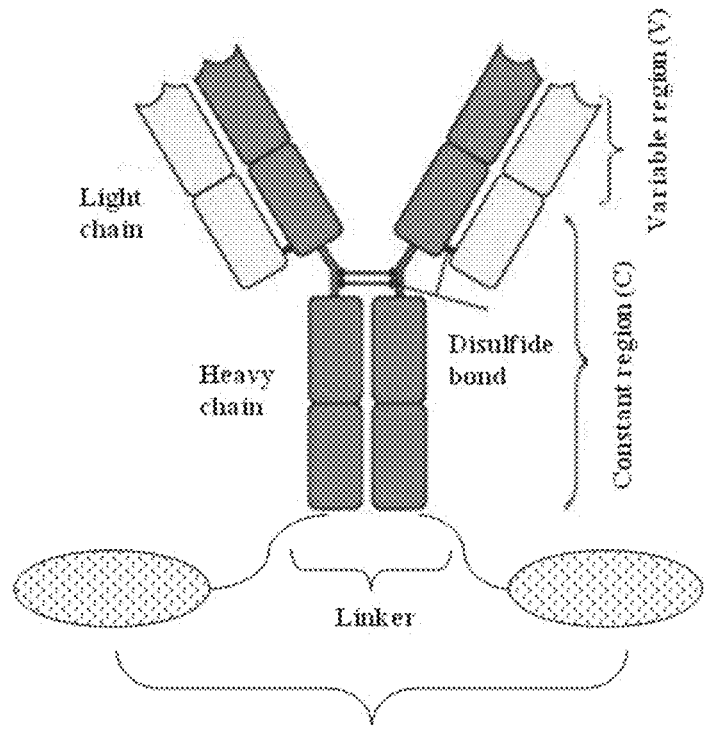
FIG. 1: Schematic diagram showing the structure of the fusion protein.

For the disclosure to be more readily understood, certain technical and scientific terms are specifically defined below. Unless specifically defined herein, all other technical and scientific terms used herein have the meaning commonly understood by one of ordinary skills in the art to which this disclosure pertains.

"Buffer" refers to a solution that is tolerated to the change of pH through the action of acid-base conjugate components. Examples of buffers that can control the pH within an appropriate range include acetate, succinate, gluconate, histidine, oxalate, lactate, phosphate, citrate, tartrate, fumarate and glycylglycine.

"Histidine salt buffer" is a buffer comprising histidine radical ions. Examples of histidine salt buffers include histidine-hydrochloride, histidine-acetate, histidine-phosphate, histidine-sulfate, and the like: preferably histidine-hydrochloride buffer. Histidine-hydrochloride buffer is prepared from histidine and hydrochloric acid.

"Citrate buffer" is a buffer that comprises citrate radical ions. Examples of the citrate buffers include citric acid-sodium citrate, citrate-potassium citrate, citrate-calcium citrate, citrate-magnesium citrate, and the like. The preferred citrate buffer is citric acid-sodium citrate.

"Succinate buffer" is a buffer that comprises succinate radical ions. Examples of the succinate buffers include succinic acid-sodium succinate, succinic acid-potassium succinate, succinic acid-succinate calcium, and the like. The preferred succinate buffer is succinic acid-sodium succinate.

"Phosphate buffer" is a buffer that comprises phosphate radical ions. Examples of the phosphate buffers include disodium hydrogen phosphate-sodium dihydrogen phosphate, disodium hydrogen phosphate-potassium dihydrogen phosphate, and the like. The preferred phosphate buffer is disodium hydrogen phosphate-sodium dihydrogen phosphate.

"Acetate buffer" is a buffer comprising acetate radical ions. Examples of acetate buffers include acetic acid-sodium acetate, histidine acetate, acetic acid-potassium acetate, acetic acid-calcium acetate, acetic acid-magnesium acetate, and the like. The preferred acetate buffer is acetic acid-sodium acetate.

"Pharmaceutical composition" refers to a mixture comprising one or more of the compounds described herein or the physiologically/pharmaceutically acceptable salts or prodrugs thereof and other chemical components, such as physiologically/pharmaceutically acceptable carrier(s) and excipient(s). The purpose of the pharmaceutical composition is to maintain the stability of the active ingredient antibody, to promote the administration to the organism, and facilitate the absorption of the active ingredient as to exert the biological activity. The "pharmaceutical composition" and "preparation" used herein are not mutually exclusive.

Unless otherwise specified, when referring to the solution form of the pharmaceutical composition described in the present disclosure, the solvent therein is water.

"Lyophilized preparation" refers to a preparation or a pharmaceutical composition obtained after a step of lyophilizing (for example, a vacuum freeze-drying step) the pharmaceutical composition in its liquid or solution form, or lyophilizing the preparation in its liquid or solution form.

The term "about" or "approximately" as used in the present disclosure means that the value is within an acceptable error range of the specific value determined by the skilled persons ordinary in the art, and the value depends partially on how it is measured or determined (i.e., the limit of the measuring system). For example, "about" or "approximately" in the art refers to a standard deviation less than one or more than one. Alternatively, "about" or "approximately" or "substantially comprising" refers to a range up to 20%. In addition, particularly for biological systems or processes, the term means an order of magnitude up to one, or up to 5 times higher than the value. Unless otherwise specified, the meaning of "about XX" or "approximately XX" or "substantially comprising XX" used in present disclosure refers to a value within an acceptable error range of the specific value "XX" (including the value "XX" itself, as well as values within an acceptable error range of the value as determined by the skilled persons ordinary in the art).

The pharmaceutical composition described in the present disclosure is capable of achieving a stable effect: the TGF-β receptor fusion protein or the pharmaceutical composition thereof substantially retains the physical stability and/or chemical stability and/or biological activity after storage: preferably, the pharmaceutical composition substantially retains the physical and chemical stability and its biological activity after storage. The shelf life is generally determined based on the predetermined shelf life of the pharmaceutical composition. There are currently many analytical techniques for measuring the stability of active ingredients, which can measure the stability after storage at a given temperature for a given period of time.

A stable pharmaceutical preparation of antibody or protein is such preparation for which no significant changes are observed under the following conditions: being stored at a refrigerated temperature (2-8° C.) for at least 3 months, preferably for 6 months, more preferably for 1 year, and even more preferably up to 2 years. In addition, stable liquid preparations include liquid preparations that exhibit desired characteristics after being stored at a temperature (including 25° C.) for 1 month, 3 months, 6 months, or stored at 40° C. for a period of 28 days.

Typical acceptable standards for stability are as follows: as measured by SEC-HPLC, usually no more than about 10%, preferably no more than about 5% of the active ingredients (such as proteins, antibodies) are degraded. By visual inspection, the pharmaceutical preparation is pale yellow nearly colorless, clear or colorless liquid, or clear to slightly milky white, or pale yellow nearly colorless clear liquid. The change of concentration, pH and osmolality of the preparation is no more than +10%. A truncation of no more than about 10%, preferably no more than about 5% is generally observed. Usually no more than about 10%, preferably no more than about 5% of aggregates are formed.

The active ingredient in the pharmaceutical preparation is deemed to "retain its physical stability", if the antibody does not show any significant increase in aggregation, precipitation and/or denaturation by visual inspection of color and/or clarity, or UV light scattering, size exclusion chromatography (SEC) and dynamic light scattering (DLS). Changes in protein conformation can be evaluated by fluorescence spectroscopy (which determines the tertiary structure of the protein) and by FTIR spectroscopy (which determines the secondary structure of the protein).

The active ingredient (such as protein or antibody) in the pharmaceutical preparation is deemed to "retain its chemical stability", if the active ingredient (such as protein or antibody) does not show any significant chemical change. By detecting and quantifying chemically altered forms of proteins or antibodies, chemical stability can be assessed. Degradation processes that often lead to a change of chemical structure of proteins include hydrolysis or truncation (evaluated by methods such as size exclusion chromatography and SDS-PAGE), oxidation (evaluated by methods such as peptide mapping combined with mass spectrometry or MALDI/TOF/MS, etc.), deamidation (evaluated by methods such as ion exchange chromatography, capillary isoelectric focusing, peptide mapping, measurement of isoaspartic acid content, etc.) and isomerization (evaluated by measurement of isoaspartic acid content, peptide mapping etc.).

An active ingredient (e.g. protein or antibody) "retains its biological stability" in the pharmaceutical preparation, if the active ingredient (e.g. protein or antibody), for a given period of time, exhibits a biological activity within a predetermined range of that when the pharmaceutical formulation is prepared. The biological activity of an active ingredient (such as a protein or antibody) can be determined, for example, by antigen-binding assay.

As used in the disclosure, the three-letter code and the single-letter code for amino acids are as described in J. Biol. Chem, 243, p 3558 (1968).

As used in the present disclosure, "antibody" refers to immunoglobulin, a four-peptide chain structure formed by two identical heavy chains and two identical light chains connected by inter-chain disulfide bond(s).

In the present disclosure, the antibody light chain described in the present disclosure further comprises light chain constant region(s), which comprise(s) a human or murine k, λ chain or a variant(s) thereof.

In the present disclosure, the antibody heavy chain described in the present disclosure further comprises heavy chain constant region(s), which comprise(s) a human or murine IgG1, IgG2, IgG3, IgG4 or variant(s) thereof.

At the N-terminus of the antibody heavy chain and light chain, a region of about 110 amino acids varies largely, which is known as variable region (Fv region): the amino acid sequence at the C-terminus is relatively stable, which is known as constant region. Variable region comprises three hypervariable regions (HVR) and four FR regions (FR) with relatively conserved sequence. Three hypervariable regions determine the specificity of an antibody, also known as complementarity determining region (CDR). Each light chain variable region (LCVR or VL) and each heavy chain variable region (HCVR or VH) is composed of three CDR regions and four FR regions, arranged from the amino terminus to the carboxyl terminus as following: FR1, CDR1, FR2, CDR2, FR3, CDR3, and FR4. Three light chain CDR regions refer to LCDR1, LCDR2, and LCDR3: three heavy chain CDR regions refer to HCDR1, HCDR2 and HCDR3. The number and location of CDR region amino acid residues in LCVR and HCVR regions of the antibody or the antigen binding fragment herein comply with known Kabat numbering criteria (LCDR1-3, HCDR1-3), or comply with Kabat and Chothia numbering criteria; Kabat numbering criteria (see Kabat et al (1991), Sequences of Proteins of Immunological Interest, the 5th edition, Public Health Service, National Institutes of Health, Bethesda, MD), and Chothia numbering criteria (see Al-Lazikani et al (1997) JMB 273:927-948).

The antibody of the present disclosure involves murine antibody, chimeric antibody and humanized antibody, preferably humanized antibody.

As used in the present disclosure, "the antibody or the binding fragment thereof" or "functional fragment" refers to Fab fragment, Fab' fragment, F(ab') 2 fragment having antigen-binding activity, as well as Fv fragment, scFv fragment binding to antigen. Fv fragment is the minimum antibody fragment which comprises all antigen-binding sites, Fv fragment comprises a heavy chain variable region and a light chain variable region, but without constant region(s). Generally, Fv antibody further comprises a polypeptide linker between the VH and VL domains to form a structure required for antigen-binding. Also, different linkers can be used to connect the variable regions of two antibodies to form a polypeptide chain, named single chain antibody or single chain Fv (sFv). As used in the present disclosure, the term "binding with PD-L1" means the ability to interact with human PD-L1. As used in the present disclosure, the term "antigen-binding site" refers to inconsecutive or consecutive three-dimensional sites on an antibody or on antigen-binding fragment thereof, which recognize a target antigen and specifically bind to the antigen.

The term "murine antibody" in the present disclosure refers to anti-human PD-L1 monoclonal antibody prepared according to the knowledge and skills in the field. During the preparation, test subject is injected with PD-L1 antigen, and then hybridoma expressing antibody which possesses desired sequence or functional characteristics is isolated.

The term "chimeric antibody" is an antibody which is formed by fusing the variable region of a non-human (such as murine) antibody with the constant region of human antibody, so as to alleviate the non-human (such as murine) antibody-induced immune response. To establish a chimeric antibody, a hybridoma secreting specific monoclonal antibody is established firstly, then genes of variable region are cloned from hybridoma cells, and then genes of constant region of human antibody are cloned as desired, the genes of non-human (such as murine) antibody variable region are ligated with genes of human constant region to form a chimeric gene which can be inserted into a human vector, and the chimeric antibody molecule is finally expressed in a eukaryotic or prokaryotic industrial system. In a preferred embodiment of the present disclosure, the light chain of the PD-L1 chimeric antibody further comprises light chain constant region(s) derived from human κ, λ chain or variant(s) thereof. The heavy chain of PD-L1 chimeric antibody further comprises heavy chain constant region(s) derived from human IgG1, IgG2, IgG3, IgG4 or variant(s) thereof. The constant region(s) of human antibody can be selected from heavy chain constant region(s) derived from human IgG1, IgG2, IgG3, IgG4 or variant(s) thereof, preferably comprises heavy chain constant region derived from human IgG2 or IgG4, or IgG4 without ADCC (antibody-dependent cell-mediated cytotoxicity) due to amino acid mutation.

The term "humanized antibody", also known as CDR-grafted antibody, refers to an antibody generated by non-human (such as murine) CDR sequences grafted onto human antibody variable region framework, i.e. antibody generated from different types of sequences of human germline antibody framework. Humanized antibody overcomes the strong anti-antibody response induced by chimeric antibody which carries a large amount of non-human (such as murine) components. Such framework sequences can be obtained from public DNA database or published references covering germline antibody gene sequences. For example, germline DNA sequences of human heavy and light chain variable region genes can be found in "VBase" human germline sequence database (available on web www.mrccpe.com.ac.uk/vbase), as well as found in Kabat, E A et al. 1991, Sequences of Proteins of Immunological Interest, the 5th Ed. To avoid the decrease of activity caused by reduced immunogenicity, the variable region framework of the human antibody is subjected to minimum back-mutation to maintain the activity. The humanized antibody of the present disclosure also refers to a humanized antibody which is further obtained by phage display for the purpose of CDR affinity maturation.

As used in the present disclosure, the term "ADCC", namely antibody-dependent cell-mediated cytotoxicity, refers to the cells expressing Fc receptors that directly kill the target cells coated by an antibody by recognizing the Fc segment of the antibody. ADCC effector function of the antibody can be reduced or eliminated by modifying the Fc segment of IgG. The modification refers to mutations on the antibody heavy chain constant region, such as mutations selected from the group consisting of N297A, L234A, L235A in IgG1; IgG2/4 chimera; or F234A/L235A mutations in IgG4.

As used in the present disclosure, "identity" indicates the degree of similarity between sequences of two polynucleotides or two polypeptides. The sequence identity in the present disclosure is at least 85%, 90% or 95%, preferably at least 95%. Non-limiting examples include, but not limited to 85%, 86%, 87%, 88%, 89%, 90%, 91%, 92%, 93%, 94%, 95%, 96%, 97%, 98%, 99%, or 100%. The comparison and determination of percent identity between two sequences can be accomplished using the default settings of the BLASTN/BLASTP algorithm available from the website of National Center For Biotechnology Institute.

The term "TGF-β receptor II" or "TGFβRII" or "transforming growth factor β receptor II" refers to binding ligands (including but not limited to TGFβ1, TGFβ2 and TGFβ3), through which the cell surface receptors trigger intracellular signaling transduction pathway.

The term "PD-L1" refers to programmed death ligand 1, also known as CD274 and B7H1. PD-L1 is a protein of 290 amino acids, having an extracellular IgV-like and IgC-like domain (amino acids 19-239 of full-length PD-L1), a transmembrane domain, and an intracellular domain of about 30 amino acids. PD-L1 is constitutively expressed on many cells such as antigen presenting cells (such as, dendritic cells, macrophages, and B cells), as well as hematopoietic and non-hematopoietic cells (such as, vascular endothelial cells, pancreatic islets, and immunologically privileged site). PD-L1 is also expressed on a variety of tumors and virus-infected cells, and is a member in the immunosuppressive milieu (Ribas 2012, NEJM 366:2517-2519). PD-L1 binds to one of two T cell co-inhibitors (PD-1 and B7-1).

The "PD-L1 antibody or antigen-binding protein thereof" of the present disclosure include any anti-PD-L1 antibodies or antigen-binding fragments thereof described in the art. The anti-PD-L1 antibody may be a PD-L1 antibody commercially available or has been disclosed in the literatures; including but not limited to BMS-936559, MPDL3280A, MEDI4736, MSB0010718C (see US2014341917, US20130034559, U.S. Pat. No. 8,779,108) and the like. The antibody may be a monoclonal antibody, a chimeric antibody, a humanized antibody, or a human antibody. The antibody fragment includes Fab fragment, Fab' fragment, F(ab') 2 fragment having antigen-binding activity, and Fv fragment and scFv fragment which binds to antigen.

As an exemplary preparation process for PD-L1 antibody of the present disclosure, it has been published in PCT application PCT/CN2016/104320 (publication No. WO2017084495), the PD-L1 antibody comprises sequences of CDRs in heavy chain variable regions as described below:

```
HCDR1:
                                    SEQ ID NO: 1
SYWMH

HCDR2:
                                    SEQ ID NO: 2
RI X1PNSG X2TSYNEKFKN

HCDR3:
                                    SEQ ID NO: 3
GGSSYDYFDY.
```

In an alternative embodiment, $X_1$ is selected from H or G; and $X_2$ is selected from G or F.

In another embodiment, an exemplary PD-L1 antibody of the present disclosure further comprises CDRs sequences of a light chain variable region as described below:

```
LCDR1:
                        SEQ ID NO: 4
RASESVSIHGTHLMH

LCDR2:
                        SEQ ID NO: 5
AASNLES

LCDR3:
                        SEQ ID NO: 6
QQSFEDPLT.
```

In another embodiment, the above CDR regions are humanized by CDR grafting strategy, and the FR of humanized light chain templates are IGKV7-3*01 and hjk2.1, the FR of humanized heavy chain templates are IGHV1-46*01 and hjh6.1, and the humanized variable region sequences are as follows:

The heavy chain variable region of humanized PD-L1 antibody:

```
                        SEQ ID NO: 7
QVQLVQSGAEVKKPGASVKVSCKASGYTFTSYWMHWVRQAPGQGLEWMG

RIX₁PNSGX₂TSYNEKFKNRVTMTRDTSTSTVYMELSSLRSEDTAVYYC

ARGGSSYDYFDYWGQGTTVTVSS;,
wherein X₁ is selected from H or G; and X₂ is
selected from G or F.
```

The light chain variable region of humanized PD-L1 antibody:

```
                        SEQ ID NO: 8
DIVLTQSPASLAVSPGQRATITCRASESVSIHGTHLMHWYQQKPGQPPKL

LIYAASNLESGVPARFSGSGSGTDFTLTINPVEANDTANYYCQQSFEDPL

TFGQGTKLEIK;
```

NOTE: The order is FR1-CDR1-FR2-CDR2-FR3-CDR3-FR4, italic portion represents FR sequence, and the underlined portion represents CDR sequence (the amino acid residues of CDRs are determined and denoted based on Kabat numbering criteria).

In another embodiment, the design for back-mutation(s) on humanized antibody of the present disclosure is performed, and the designed back mutations are shown in Table 1 below:

TABLE 1

| back-mutation design | | | |
|---|---|---|---|
| VL | | VH | |
| VL.1 | grafted | VH.1 | grafted |
| VL.1A | Y91F | VH.1A | T74K |
| VL.1B | Y91F, G72E | VH.1B | T74K, R72V, M48I, M70L |
| VL.1C | Y91F, G72E, T22S | VH.1C | T74K, R72V, M48I, M70L, R38Q |

TABLE 1-continued

| back-mutation design | | |
|---|---|---|
| VL | | VH |
| | VH.1D | T74K, R72V, M48I, M70L, R38Q, L83F |
| | VH.1E | T74K, R72V, M48I, M70L, R38Q, L83F, V68A, V79A |

Note:
For example, Y91F indicates a bck-mutation from Y to F at position 91 according to natural numbering.
"Grafted" indicates that the murine antibody CDR is implanted onto human germline FR sequences.

New humanized antibodies can be obtained by various mutation combinations of heavy chain and light chain shown in Table 1.

In another aspect of the disclosure, an embodiment for constructing a humanized clone is provided, as follows:

Primers were designed, and VH/VK gene fragments of each humanized antibody were constructed by PCR, and then inserted into expression vector pHr (having signal peptide and constant region gene (CH1-Fc/CL) fragment) to perform homologous recombination, in order to construct a full-length antibody expression vector: VH-CH1-Fc-pHr/VK-CL-pHr.

1. Primer Design:

The online software DNAWorks (v3.2.2) (http://helixweb.nih.gov/dnaworks/) was used to design multiple primers for synthesis of VH/VK comprising gene fragments required for recombination: 5'-30 bp signal peptide+VH/VK+30 bp CH1/CL-3'.

2. Fragment Splicing:

According to manuals for Primer STAR GXL DNA polymerase from TaKaRa, using the primers designed above, VH/VK comprising gene fragments required for recombination was obtained by two-step PCR amplification.

3. Construction and Enzymatic Digestion of Expression Vector pHr (Having Signal Peptide and Constant Region Gene (CH1-FC/CL) Fragment):

The expression vector pHr (having signal peptide and constant region gene (CH1-FC/CL) fragment) was designed and constructed by using some special restriction endonuclease, such as BsmBI which recognizes the distinctive feature between the sequence and restriction site. The vector was digested using BsmBI, and then the digested fragments were extracted by using gel and stored for use.

4. Recombinant Construction of Expression Vector VH-CH1-Fc-pHr/VK-CL-pHr

VH/VK comprising gene fragments required for recombination and expression vector pHr (having signal peptide and constant region gene (CH1-Fc/CL) fragment) that has been digested with BsmBI were added into DH5H competent cells at a ratio of 3:1, incubated at 0° C. on ice for 30 min, heat-shocked at 42° C. for 90s, 5 volumes of LB medium was added, and then incubated at 37° C. for 45 min, then plated onto LB-Amp plate, cultured at 37° C. overnight. Single clone was picked for sequencing and a clone of interest was obtained.

5. The plasmid was constructed according to the design in the present example, then the purified protein was expressed, and the affinity of the obtained protein was measured by the detection described in SPR Example.

6. Finally, the affinity of the humanized back-mutation mutant(s) or hybridoma antibodies to human PD-L1-his was measured by BIACORE, the humanized back-mutation sites and combinations of sequences obtained from screening are as follows:

The heavy chain variable region of PD-L1 antibody:

SEQ ID NO: 9

*QVQLVQSGAEVKKPGASVKVSCKASGYTFTS*YWMH*WVRQAPGQGLEWM*

*GR*IGPNSGFTSYNEKFKN*RVTMTRDTSTSTVYMELSSLRSEDTAVYYC*

*AR*GGSSYDYFDY*WGQGTTVTVSS;* wherein HCDR2 is as shown in RIGPNSGFTSYNEKFKN SEQ ID NO: 10, i.e., $X_1$ in SEQ ID NO: 7 is G, and $X_2$ in SEQ ID NO: 7 is F:

The light chain variable region of PD-L1 antibody:

SEQ ID NO: 11

*DIVLTQSPASLAVSPGQRATITC*RASESVSIHGTHLMH*WYQQKPGQPPKLL*

*IY*AASNLES*GVPARFSGSGSGTDFTLTINPVEAEDTANYYC*QQSFEDPLT

*FGQGTKLEIK;*

NOTE: The order is FR1-CDR1-FR2-CDR2-FR3-CDR3-FR4, italic portion represents FR sequence, and the underlined portion represents CDR sequence (the amino acid residues of CDRs are determined and denoted based on Kabat numbering criteria).

In another aspect of the present disclosure, an embodiment for constructing and expressing an anti-PD-L1 human IgG4 type antibody is provided, and further provided is a PD-L1 antibody used for construction of fusion protein. The PD-L1 antibody can also be used as a control molecule in the Test Examples of the present disclosure.

Since PD-L1 is also expressed in activated T cells, therefore the use of wild-type IgG1 constant regions can cause Fc-mediated effects (such as ADCC and CDC), which could result in the reduction of activated T cells. The present disclosure selected mutated IgG4 to obtain antibodies without ADCC and CDC. The clone obtained by affinity maturation was converted into IgG4 type, and the core hinge region of IgG4 comprises S228P mutation (corresponding to the position 227 in the natural sequence of SEQ ID NO: 12). F234A (corresponding to the position 233 in the natural sequence of SEQ ID NO: 12) and L235A mutation (corresponding to the position 234 in the natural sequence of SEQ ID NO: 12) were further introduced (mAbs 4:3, 310-318; May/June 2012). At the same time, in order to avoid breakage occurred at the C-terminus of the antibody heavy chain when the linker peptide (which is used to link the TGF-βRII extracellular domain) was introduced, K on the end position of the PD-L1 antibody heavy chain was further mutated to A (corresponding to the last position in the natural sequence of SEQ ID NO: 12), so as to increase the stability of the fusion protein. The PD-L1 antibody sequence of the present disclosure used for fusion protein construction is as follows:

PD-L1 antibody heavy chain: IgG4 (AA) (S228P)

SEQ ID NO: 12

QVQLVQSGAEVKKPGASVKVSCKASGYTFTSYWMHWVRQAPGQGLEWMGR

IGPNSGFTSYNEKFKNRVTMTRDTSTSTVYMELSSLRSEDTAVYYCARGG

SSYDYFDYWGQGTTVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCP*P*CPAPEAAGGPSVFLFPPKPKDTL

-continued
MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGA;

NOTE: The underlined portion is the heavy chain variable region sequence, and the un-underlined portion is the heavy chain constant region sequence (the portion in italics is the mutation site);

PD-L1 antibody light chain:

SEQ ID NO: 13

DIVLTQSPASLAVSPGQRATITCRASESVSIHGTHLMHWYQQKPGQPPKLL

IYAASNLESGVPARFSGSGSGTDFTLTINPVEAEDTANYYCQQSFEDPLTF

GQGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC;

NOTE: The underlined portion is the light chain variable region sequence, and the un-underlined portion is the light chain constant region sequence.

As used in the present disclosure, a fusion protein described in the present disclosure is a protein product obtained by co-expressing two genes via DNA recombination technology. Methods for producing and purifying antibodies and antigen-binding fragments are well known in the art and can be found (e.g., in Antibodies, A Laboratory Manual, Cold Spring Harbor, chapters 5-8 and 15). For example, mice can be immunized with human PD-L1 or fragments thereof, and the resulting antibodies can then be re-natured, purified, and sequenced for amino acid sequences by using conventional methods well known in the art. Antigen-binding fragments can also be prepared by conventional methods. The antibody or antigen binding fragments of the present disclosure are engineered to graft CDRs derived from non-human antibody into one or more human FRs. By aligning against the database of IMGT human antibody variable region germline using MOE software, human framework germline sequences can be obtained from ImMunoGeneTics (IMGT) website http://imgt.cines.fr, or from The Immunoglobulin Facts Book, 2001, ISBN 012441351.

The engineered antibodies or antigen binding fragments of the present disclosure may be prepared and purified using known methods. For example, cDNA sequences encoding a heavy chain and a light chain may be cloned and engineered into a GS expression vector. The engineered immunoglobulin expression vector may then be stably transfected in CHO cells. As a more recommended method known in the art, mammalian expression system will result in glycosylation of antibody, typically at highly conserved N-terminus sites in the Fc region. Stable clones may be obtained by expression of an antibody specifically binding to human PD-L1. Positive clones may be expanded in serum-free culture medium for antibody production in bioreactors. Culture medium, into which the antibody has been secreted, may be purified by conventional techniques. For example, the medium may be loaded onto a Protein A or G Sepharose FF column that has been equilibrated with a compatible buffer. The column is washed to remove nonspecific binding components. The bound antibody is eluted by pH gradient and antibody fractions are detected by SDS-PAGE, and then collected.

The antibody may be filtered and concentrated using common techniques. Soluble aggregate and multimers may be effectively removed by common techniques, including size exclusion or ion exchange. The product may be immediately frozen, for example at −70° C., or may be lyophilized.

The "immuno-modulatory molecule" of the present disclosure can be used to attenuate the immune tolerance of cancer cells. The present disclosure uses a truncated form of the TGF-βRII extracellular domain as the immuno-modulatory molecule in the fusion protein. "TGF-β receptor II (TGF-βRII)" binds to ligands TGF-β1 and TGF-β3 with high affinity. The TGF-β RII/TGF-β complex recruits TGF-β RI to form a signal transduction complex (Won et al, Cancer Res. 1999; 59: 1273-7). The TGF-βRII extracellular domain is a 136 amino acid residue peptide from the N-terminus of TGF-βRII extracellular, an exemplary example of which is shown in SEQ ID NO: 14. Other variants of about 136 amino acids in length and derived from human TGF-βRII extracellular domain, which capable of binding to TGF-β1 and TGF-β3, also belong to the TGF-βRII extracellular domain of the disclosure. The present disclosure has found that the structure and function of the N-terminus consecutive truncated form of the TGF-βRII extracellular domain is more stable than that of the un-truncated molecule. A fusion protein comprising the N-terminus un-truncated form of TGF-βRII extracellular domain (a polypeptide shown as aa. 1-136 of SEQ ID NO: 14) is susceptible to be broken. In particular, the TGF-β RII extracellular domain which is truncated by less than 26 consecutive amino acids from N terminus is more stable: preferably, the TGF-β RII extracellular domain which is truncated by 14-26, and more preferably, truncated by 14-21 consecutive amino acids from N terminus, has a higher expression level; and most preferably, truncated by 19 or 21 consecutive amino acids.

The term "TGF-β receptor fusion protein" is a fusion protein comprising TGF-β receptor. In some embodiments, the TGF-β receptor fusion protein of the present disclosure is the TGF-β receptor fusion protein described in the international patent application PCT/CN2018/086451 (WO 2018205985A1). The full content of WO 2018205985A1 is incorporated entirely into the present disclosure. In some embodiments, the TGF-β receptor fusion protein is a PD-L1 antibody/TGF-βRII extracellular domain fusion protein (PD-L1/TGF-β trap), with the TGF-βRII extracellular domain served as the immuno-modulatory molecule part of the fusion protein, the PD-L1 antibody is served as the targeting part of the fusion protein, the TGF-βRII extracellular domain (for example, shown as SEQ ID NO: 14, 15, 16 or 17) is connected to the C-terminus (also known as carboxyl end) of the heavy chain of the PD-L1 antibody by a linker sequence (for example (G4S)xG, x is 3-6), to form a fusion sequence, and the fusion sequence is connected with the light chain of the PD-L1 antibody through inter-chain disulfide bond(s) to form PD-L1/TGF-β trap fusion protein finally, the structure is shown in FIG. 1. In some embodiments, the TGF-β receptor fusion protein is the fusion protein described in Table 2 of Example 1 of the disclosure.

The term "linker" or "linker sequence" refers to a connecting peptide sequence used to connect protein domains, usually with a certain degree of flexibility, and the use of linkers will not lead to the loss of original function of the protein domain. In some embodiments of the present disclosure, the linker sequence is $(G_4S)_xG$, wherein x is 3-6, for example, the linker sequence is a polypeptide such as: $(G_4S)_3G$, $(G_4S)_4G$, $(G_4S)_5G$, or $(G_4S)_6G$.

"Conservative modification" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skilled in the art recognize that, in general, single amino acid substitution in a non-essential region of a polypeptide does not substantially alter biological activity (see, e.g., Watson et al. (1987) Molecular Biology of the Gene, The Benjamin/Cummings Pub. Co., p 224 (4th edition)). In addition, substitutions of structurally or functionally similar amino acids are less likely to disrupt biological activity.

"Optional" or "optionally" means that the event or situation that follows may occur, but not necessarily, and the description includes the instances in which the event or circumstance does or does not occur. For example, "optionally comprising 1-3 antibody heavy chain variable region(s)" means the antibody heavy chain variable region with specific sequence can be present, but not necessarily.

"Administration", "administrating" and "treatment," as they apply to an animal, human, experimental subject, cell, tissue, organ, or biological fluid, refer to the contact of an exogenous pharmaceutical, therapeutic, diagnostic agent or composition to the animal, human, subject, cell, tissue, organ or biological fluid. "Administration", "administrating" and "treatment" can refer to, e.g., therapeutic, pharmacokinetic, diagnostic, research and experimental methods. Treatment of a cell encompasses contacting a reagent to a cell, as well as contacting a reagent to a fluid, where the fluid is in contact with the cell. "Administration", "administrating" and "treatment" also mean in vitro and ex vivo treatments, e.g., of a cell, by a reagent, diagnostic, binding composition, or by another cell. "Administration" or "treatment" as it applies to a human, veterinary or research subject, refers to therapeutic treatment, prophylactic or preventative measures, to research and diagnostic applications.

"Treat" means to administer a therapeutic agent, such as a composition of the present disclosure, internally or externally, to a subject having one or more disease symptoms for which the agent has known therapeutic activity. Typically, the agent is administered in an amount effective to alleviate one or more disease symptoms in the subject or population to be treated, to induce the regression of or prevent the progression of such symptom(s) at a clinically measurable degree. The amount of a therapeutic agent that is effective to alleviate any particular disease symptom (also referred to as the "therapeutically effective amount") may vary according to factors such as the disease state, age, and weight of the subject, and the ability of the agent to elicit a desired response in the subject. Whether a disease symptom has been alleviated can be assessed by any clinical measurement typically used by physicians or other skilled healthcare providers to assess the severity or progression status of the symptom. Although an embodiment of the present disclosure (e.g., a treatment method or article of manufacture) may not be effective in alleviating the target disease symptom(s) in every subject, it should alleviate the target disease symptom(s) in a statistically significant number of subjects as determined by any statistical test known in the art, such as the Student's t-test, the chi-square test, the U-test according to Mann and Whitney, the Kruskal-Wallis test (H-test), Jonckheere-Terpstra-test and the Wilcoxon-test.

"Effective amount" encompasses an amount sufficient to ameliorate or prevent a symptom or sign of the medical condition. Effective amount also means an amount sufficient to allow or facilitate diagnosis. An effective amount for a particular subject or veterinary subject may vary depending on factors, such as the condition being treated, the overall health condition of the subject, the route and dosage of administration and the severity of side effects. An effective amount can be the maximal dosage or dosing protocol that avoids significant side effects or toxic effects.

"Tm value" refers to a temperature at which the thermal denaturation occurs to a protein, that is, the temperature at which half of the protein is unfolded. At this time, the spatial structure of the protein is destroyed. Therefore, the higher the Tm value, the higher the thermal stability of the protein.

"Substitution" refers to a replacement of the solvent system that dissolves the antibody protein. For example, the high salt or hypertonic solvent system comprising the antibody protein is replaced using physical operation against a buffer system for stable preparation, so that the antibody protein can be present in the stable preparation. The physical operation includes but not limited to ultrafiltration, dialysis or reconstitution following centrifugation.

DETAILED DESCRIPTION OF THE INVENTION

Hereinafter, the present disclosure is further described with reference to examples, test examples or preparation examples. However, the examples, test examples or preparation examples are only for illustrative purpose, the scope of the present disclosure is not limited thereto.

In the examples, test examples or preparation examples of the present disclosure, where specific conditions are not described, they are generally conducted under conventional conditions or under conditions proposed by the material or product manufacturers. Where the source of the reagents is not specifically indicated, the reagents are commercially available conventional reagents.

EXAMPLES

Example 1: Cloning and Expression of Fusion Protein PD-L1/TGF-β Trap

The TGF-βRII extracellular domain (full length or truncated form of SEQ ID NO: 14) was used as the portion for immuno-modulatory molecule in the fusion protein, and the PD-L1 antibody is used as a targeting portion of the fusion protein to form a PD-L1 antibody/TGF-βRII extracellular domain fusion protein (PD-L1/TGF-β trap).

It was surprisingly found that the truncated form of the TGF-βRII extracellular domain is relatively stable, especially more stable after being truncated by less than 26 amino acids from its N-terminus, preferably, higher expression level and more stable structure are obtained after being truncated by 14-26 amino acids, more preferably being truncated by 14-21 consecutive amino acids from N-terminus, and more preferably being truncated by 14, 19 or 21 consecutive amino acids from N-terminus.

The sequences of the non-limiting examples of TGF-βRII extracellular domain and its truncated form in the present disclosure are as follows:

Sequence of TGF-βRII extracellular domain: ECD (1-136)
SEQ ID NO: 14
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPD;

TGF-β RII extracellular domain sequence, with a truncation or deletion of 19 amino acids at the N-terminus: ECD (20-136)
SEQ ID NO: 15
GAVKFPQLCKFCDVRFSTCDNQKSCMSNCSITSICEKPQEVCVAVWRKNDE
NITLETVCHDPKLPYHDFILEDAASPKCIMKEKKKPGETFFMCSCSSDECN
DNIIFSEEYNTSNPD;

TGF-β RII extracellular domain sequence, with a truncation or deletion of 21 amino acids at the N-terminus: ECD (22-136)
SEQ ID NO: 16
VKFPQLCKFCDVRFSTCDNQKSCMSNCSITSICEKPQEVCVAVWRKNDENI
TLETVCHDPKLPYHDFILEDAASPKCIMKEKKKPGETFFMCSCSSDECNDN
IIFSEEYNTSNPD;

TGF-β RII extracellular domain sequence, with a truncation or deletion of 14 amino acids at the N-terminus: ECD (15-136)
SEQ ID NO: 17
VTDNNGAVKFPQLCKFCDVRFSTCDNQKSCMSNCSITSICEKPQEVCVAVW
RKNDENITLETVCHDPKLPYHDFILEDAASPKCIMKEKKKPGETFFMCSCS
SDECNDNIIFSEEYNTSNPD.

As an example, the heavy chain C-terminus amino acid of the PD-L1 antibody of the present disclosure (a PD-L1 antibody, wherein the heavy chain shown as SEQ ID NO: 12, and light chain shown as SEQ ID NO: 13) was ligated to the TGF-βRII extracellular domain with varying lengths by linker $(G_4S)_xG$ (x is 3-6), by homologous recombination technique, and was conventionally expressed in 293 expression system together with the light chain of PD-L1 antibody, and the obtained fusion proteins are shown in Table 2:

TABLE 2

| Fusion protein of PD-L1 antibody/TGF-βRII extracellular domain | | |
|---|---|---|
| Fusion protein | Sequence description | the number of consecutive amino acid deleted at N-terminus |
| Fusion protein 1 | Ab-$(G_4S)_4$G-ECD (1-136) | Without deletion |
| Fusion protein 2 | Ab-$(G_4S)_3$G-ECD (15-136) | 14 |
| Fusion protein 3 | Ab-$(G_4S)_3$G-ECD (15-136, N19A) | 14 |
| Fusion protein 4 | Ab-$(G_4S)_3$G-ECD (20-136) | 19 |
| Fusion protein 5 | Ab-$(G_4S)_3$G-ECD (22-136) | 21 |
| Fusion protein 6 | Ab-$(G_4S)_3$G-ECD (27-136) | 26 |
| Fusion protein 7 | Ab-$(G_4S)_4$G-ECD (15-136) | 14 |
| Fusion protein 8 | Ab-$(G_4S)_4$G-ECD (15-136, N19A) | 14 |
| Fusion protein 9 | Ab-$(G_4S)_4$G-ECD (20-136) | 19 |
| Fusion protein 10 | Ab-$(G_4S)_4$G-ECD (22-136) | 21 |
| Fusion protein 11 | Ab-$(G_4S)_4$G-ECD (27-136) | 26 |
| Fusion protein 12 | Ab-$(G_4S)_5$G-ECD (15-136) | 14 |
| Fusion protein 13 | Ab-$(G_4S)_5$G-ECD (15-136, N19A) | 14 |

TABLE 2-continued

Fusion protein of PD-L1 antibody/TGF-βRII extracellular domain

| Fusion protein | Sequence description | the number of consecutive amino acid deleted at N-terminus |
|---|---|---|
| Fusion protein 14 | Ab-(G₄S)₅G-ECD (20-136) | 19 |
| Fusion protein 15 | Ab-(G₄S)₅G-ECD (22-136) | 21 |
| Fusion protein 16 | Ab-(G₄S)₅G-ECD (27-136) | 26 |
| Fusion protein 17 | Ab-(G₄S)₆G-ECD (27-136) | 26 |

Note: Ab represents PD-L1 antibody of the present disclosure (the heavy chain shown as SEQ ID NO: 12, and light chain shown as SEQ ID NO: 13); ECD (n-136) in Sequence Description represents the full-length or truncated form of the TGF-βRII extracellular domain; n represents the starting number of amino acid after truncation of the TGF-βRII extracellular domain. The structure of the fusion protein of the present disclosure is shown in FIG. 1; N19A indicates that the amino acid at position 19 of the full-length TGF-βRII extracellular domain (SEQ ID NO: 14) is mutated from N to A.

The nucleotide sequence encoding the PD-L1 antibody, the nucleotide sequence encoding the TGF-βRII extracellular domain, and the nucleotide sequence of the linker protein fragment ((G₄S)ₓG) were obtained by conventional technique in the art. The C-terminus nucleotide of the PD-L1 antibody was ligated through linker protein to the N-terminus nucleotide of the TGF-βRII extracellular domain with different length by homologous recombination technique, and then cloned into the Phr-BsmbI vector. Recombinant PD-L1/TGF-β trap was expressed in 293 cells and purified as described in Example 2. The purified protein can be used in the experiments of the following examples.

Example 2: Purification of PD-L1/TGF-β Trap Fusion Protein

The cell culture medium was centrifuged at high speed, and the supernatant was collected, and the first step of purification was performed by affinity chromatography. The chromatographic medium is Protein A or derived filler that interacts with Fc, such as GE's Mabselect. The equilibration buffer was 1×PBS (137 mmol/L NaCl, 2.7 mmol/L KCl, 10 mmol/L Na₂HPO₄, 2 mmol/L KH₂PO₄, pH7.4). After equilibrating 5× column volumes, the cell supernatant was loaded for binding, and the flow rate was controlled so that the sample was allowed to be remained on the column for ≥1 min. After sample was loaded, the column was washed with 1×PBS (pH 7.4) until the A280 UV absorption was reduced to baseline. Then, the column was washed with 0.1 M glycine (pH 3.0) elution buffer, and the eluted peak was collected according to the A280 UV absorption peak, and the collected eluted sample was neutralized with 1 M Tris (pH 8.5).

The neutralized eluted sample was concentrated by ultrafiltration, and then subjected to size exclusion chromatography, the buffer was 1×PBS, and the column was XK26/60 Superdex 200 (GE). The flow rate was controlled at 4 ml/min, the loading volume was less than 5 ml, and the target protein peak was pooled according to A280 UV absorption. The purity of the collected protein was greater than 95% as identified by SEC-HPLC, and was verified by LC-MS. The verified sample was aliquoted for use. The PD-L1/TGF-β trap was obtained.

The performance and beneficial effect of PD-L1/TGF-β trap fusion protein in the present disclosure are verified by biochemical test methods as indicated below:

Test Example (Biological Evaluation In Vivo, In Vitro)

Test Example 1: In Vitro ELISA Detection of PD-L1/TGF-β Trap Binding to TGF-β1

The detection process is described as follows:
- a. 96-well plates were coated with 100 μl/well of human TGF-β1 (8915LC, CST) at a concentration of 1 μg/ml at 4° C. overnight.
- b. Washing 3 times with 250 μl of 1×PBST, 250 μl of 5% milk PBS was added for blocking at 37° C. for 2 hours.
- c. Washing 3 times with 250 μl of 1×PBST, gradient dilutions of PD-L1/TGF-β trap were added, and TGF-β trap was used as positive control and incubated for 1 hour at 37° C.
- d. Washing 3 times with 250 μl 1×PBST.
- e. 100 μl of Anti-human Fc antibody-HRP (1:4000) was added to each well and incubated for 40 minutes at 37° C.
- f. 100 μl of TMB was added into each well, incubated for 10 minutes at room temperature, and the reaction was stopped by adding 100 μl of 1 M H₂SO₄.
- g. The absorbance at 450 nm was measured on a microplate reader, and the data was analyzed by Graphpad Prism 5.

Figure 2:
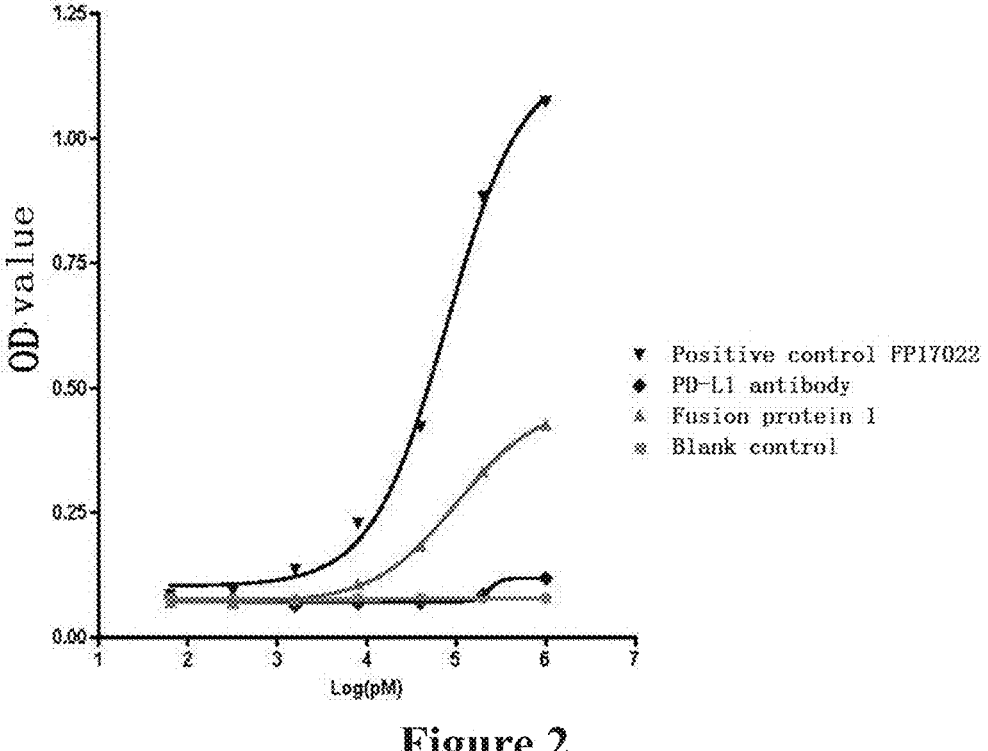
FIG. 2: Results showing the binding of fusion proteins to human TGF-β1 in vitro.
Figure 3:
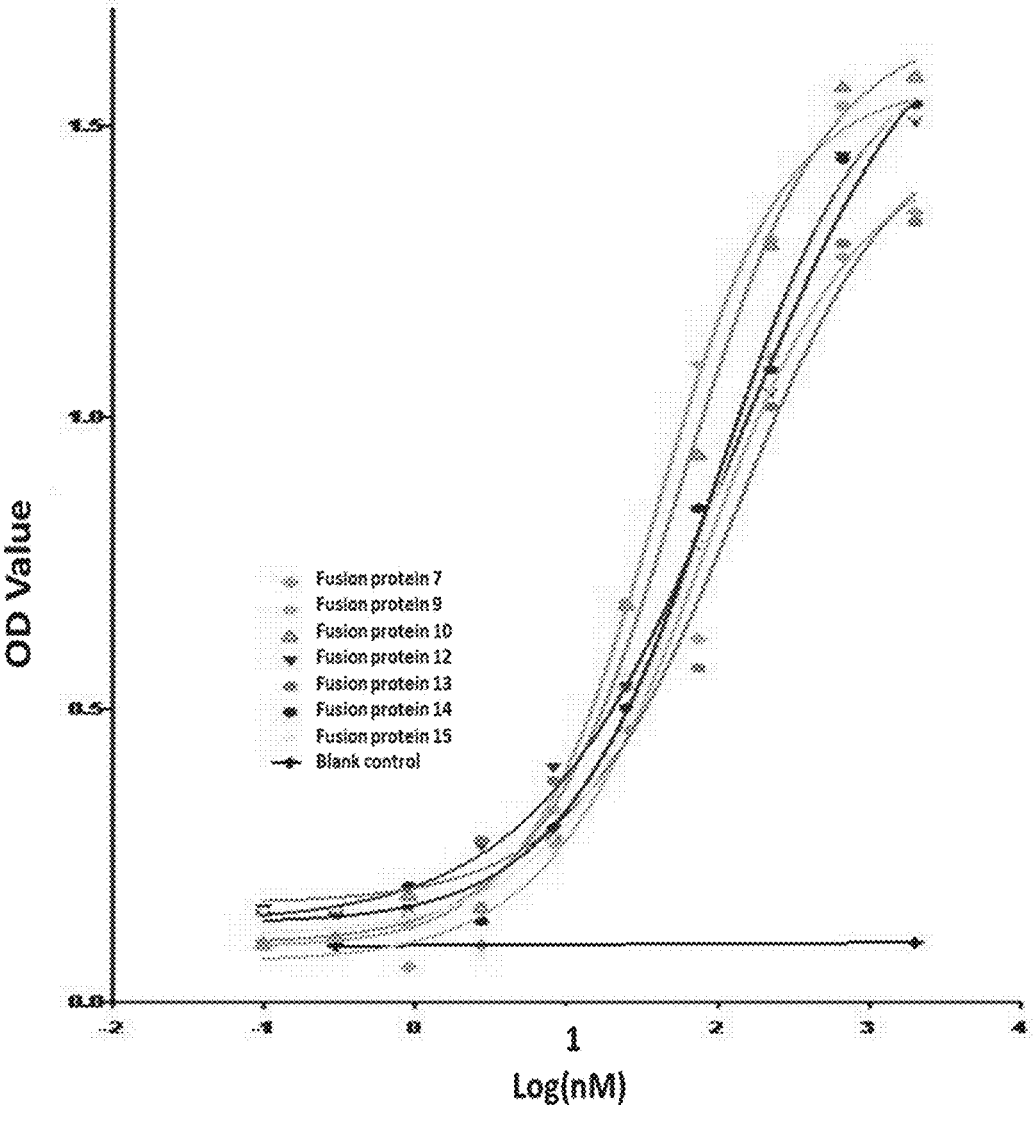
FIG. 3: Results showing the binding of fusion proteins to human TGF-β1 in vitro.

The results of binding of the fusion proteins to human TGF-β1 in vitro are shown in FIGS. 2 and 3. The ELISA showed that fusion protein 1 in Table 2 did not retain the binding activity to human TGF-β1. Mass spectrometry analysis showed that fusion protein 1 (i.e., the un-truncated form of TGF-βRII extracellular domain (1-136)) was unstable, and it was easily broken in the heavy chain TGF-βRII, and positive control has the same defect. The fusion proteins comprising the N-terminus truncated form of the extracellular domain of TGFβRII, such as fusion proteins 7, 9, 10, 12-15, specifically bind to human TGF-β1.

Test Example 2: In Vitro ELISA Detection of PD-L1/TGF-β Trap Binding to PD-L1

```
Antigen used for detection: PD-L1-His
                                        SEQ ID NO: 18
FTVTVPKDLYVVEYGSNMTIECKFPVEKQLDLAALIVYWEMEDKNIIQFVH

GEEDLKVQHSSYRQRARLLKDQLSLGNAALQITDVKLQDAGVYRCMISYGG

ADYKRITVKVNAPYNKINQRILVVDPVTSEHELTCQAEGYPKAEVIWTSSD

HQVLSGKTTTTNSKREEKLFNVTSTLRINTTTNEIFYCTFRRLDPEENHTA

ELVIPELPLAHPPNEREQKLISEEDLHHHHHH.
```

The detection process is described as follows:
- a. 96-well plates were coated with 100 μl/well of human PD-L1-His (SEQ ID NO: 18) at a concentration of 5 μg/ml at 4° C. overnight.
- b. Washing 3 times with 250 μl of 1×PBST, 250 μl of 5% milk PBS was added for blocking at 37° C. for 2 hours.
- c. Washing 3 times with 250 μl of 1×PBST, gradient dilutions of PD-L1/TGF-β trap, and PD-L1 antibody as positive control were added, and incubated for 1 hour at 37° C.

d. Washing 3 times with 250 μl 1×PBST.

e. 100 μl of Anti-human Fc antibody-HRP (1:4000) was added into each well and incubated for 40 minutes at 37° C.

f. 100 μl of TMB was added into each well, incubated for 10 minutes at room temperature, and the reaction was stopped by adding 100 μl of 1 M $H_2SO_4$.

g. The absorbance at 450 nm was measured on a microplate reader, and the data was analyzed by Graphpad Prism 5.

Figure 4:
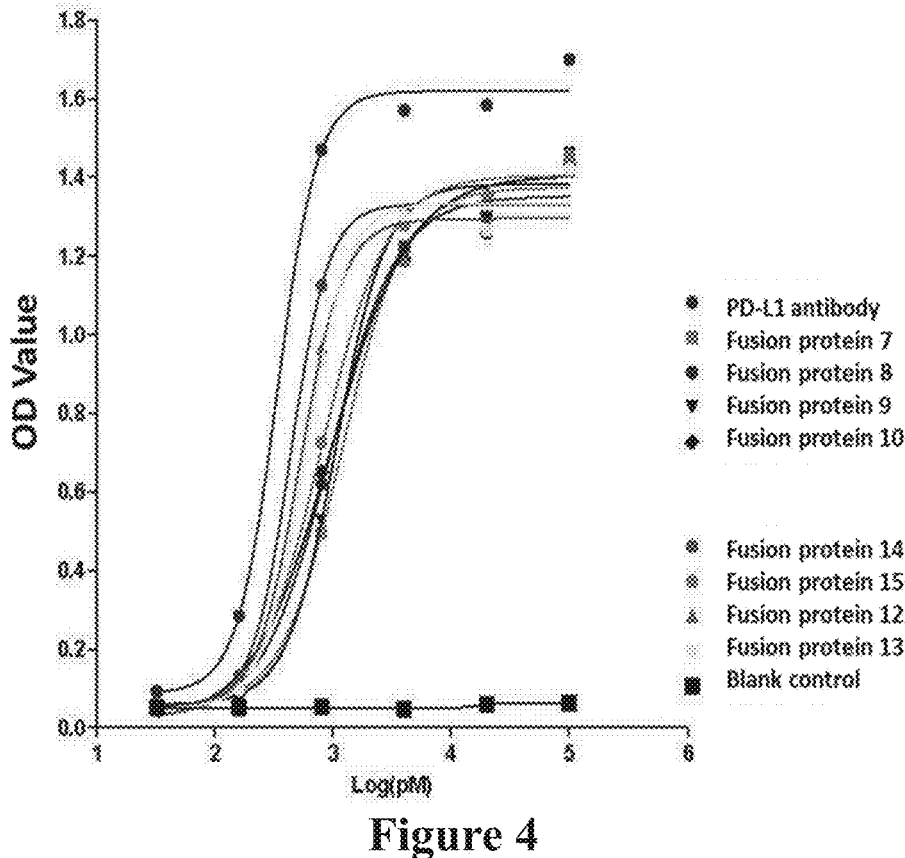
FIG. 4: Results showing the binding of fusion proteins to human PD-L1 in vitro.

The results of binding of the fusion proteins of the present disclosure to human PD-L1 in vitro are shown in FIG. 4. The ELISA showed that all fusion proteins retained the binding activity to human PD-L1.

Test Example 3: Blocking Detection of PD-1/PD-L1 Pathway In Vitro

1. Test Purpose:

In order to investigate the blocking effect of PD-L1/TGF-β trap on PD-1/PD-L1 signaling pathway, cell-based antibody blocking experiment was performed on cells carrying human PD-1 and PD-L1 receptor molecules which were constructed by Promaga, respectively.

2. Test Samples

① PD-L1 antibody with heavy chain shown as SEQ ID NO: 12, and light chain shown as SEQ ID NO: 13;

② Control 1 (20T-Fc): ECD (20-136)-Fc, a fusion protein comprising truncated TGF-βRII extracellular domain fragment ECD (20-136) and Fc, and the sequence is as follows:

```
                                        SEQ ID NO: 19
GAVKFPQLCKFCDVRFSTCDNQKSCMSNCSITSICEKPQEVCVAVWRKNDE

NITLETVCHDPKLPYHDFILEDAASPKCIMKEKKKPGETFFMCSCSSDECN

DNIIFSEEYNTSNPDAESKYGPPCPPCPAPEAAGGPSVFLFPPKPKDTLMI

SRTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFL

YSRLTVDKSRWQEGNVFSCSVMHEALHNHYTQKSLSLSLG;
```

③ Control 2 (22T-Fc): ECD (22-136)-Fc, a fusion protein of truncated TGF-βRII extracellular domain fragment ECD (22-136) and Fc, and the sequence is as follows:

```
                                        SEQ ID NO: 20
VKFPQLCKFCDVRFSTCDNQKSCMSNCSITSICEKPQEVCVAVWRKNDENI

TLETVCHDPKLPYHDFILEDAASPKCIMKEKKKPGETFFMCSCSSDECNDN

IIFSEEYNTSNPDAESKYGPPCPPCPAPEAAGGPSVFLFPPKPKDTLMISR

TPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLYS

RLTVDKSRWQEGNVFSCSVMHEALHNHYTQKSLSLSLG;
```

④ TGF-β receptor fusion protein prepared in Example 1 of the present disclosure: the fusion protein 9, fusion protein 15:

In fusion protein 9, the fusion peptide sequence of PD-L1 antibody heavy chain-$(G_4S)_4$G-TGF-β RII ECD (20-136) is as follows:

```
                                        SEQ ID NO: 23
QVQLVQSGAEVKKPGASVKVSCKASGYTFTSYWMHWVRQAPGQGLEWMGR

IGPNSGFTSYNEKFKNRVTMTRDTSTSTVYMELSSLRSEDTAVYYCARGG

SSYDYFDYWGQGTTVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEAAGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGAGGGG

SGGGGSGGGGSGGGGSGGAVKFPQLCKFCDVRFSTCDNQKSCMSNCSITS

ICEKPQEVCVAVWRKNDENITLETVCHDPKLPYHDFILEDAASPKCIMKE

KKKPGETFFMCSCSSDECNDNIIFSEEYNTSNPD;
```

NOTE: The regular font is the sequence of the heavy chain of the PD-L1 antibody, the italic is the linker sequence, and the underline is the sequence of the truncated fragment ECD (20-136) of the TGF-βRII extracellular region.

The light chain sequence of the PD-L1 antibody in fusion protein 9 is as follows:

```
                                        SEQ ID NO: 13
DIVLTQSPASLAVSPGQRATITCRASESVSIHGTHLMHWYQQKPGQPPKLL

IYAASNLESGVPARFSGSGSGTDFTLTINPVEAEDTANYYCQQSFEDPLTF

GQGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC;
```

The fusion peptide sequence of PD-L1 antibody heavy chain-(GAS) s G-TGF-β RII ECD (22-136) in fusion protein 15 is as follows:

```
                                        SEQ ID NO: 24
QVQLVQSGAEVKKPGASVKVSCKASGYTFTSYWMHWVRQAPGQGLEWMGR

IGPNSGFTSYNEKFKNRVTMTRDTSTSTVYMELSSLRSEDTAVYYCARGG

SSYDYFDYWGQGTTVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEAAGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGAGGGG

SGGGGSGGGGSGGGGSGGGGSGVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD;
```

NOTE: The regular font is the sequence of the heavy chain of the PD-L1 antibody, the italic is the linker sequence, and the underline is the sequence of the truncated fragment ECD (22-136) of the TGF-βRII extracellular region.

The light chain sequence of the PD-L1 antibody in fusion protein 15 is as follows:

```
                                    SEQ ID NO: 13
DIVLTQSPASLAVSPGQRATITCRASESVSIHGTHLMHWYQQKPGQPPKLL

IYAASNLESGVPARFSGSGSGTDFTLTINPVEAEDTANYYCQQSFEDPLTF

GQGTKLEIKRTVAAPSVFIFPPSDEQLKSGTASVVCLLNNFYPREAKVQWK

VDNALQSGNSQESVTEQDSKDSTYSLSSTLTLSKADYEKEIKVYACEVTHQ

GLSSPVTKSFNRGEC;
```

⑤ human IgG: blank control, human immunoglobulin obtained from mixed normal human serum by purification using a conventional affinity chromatography method such as Protein A;

⑥ Positive control (FP17022): fusion protein of PD-L1 antibody 2/TGF-βRII extracellular domain;

The amino acid sequence of PD-L1 antibody 2 light chain in FP17022 fusion protein:

```
                                    SEQ ID NO: 21
QSALTQPASVSGSPGQSITISCTGTSSDVGGYNYVSWYQQRPGKAPKLMIY

DVSNRPSGVSNRFSGSKSGNTASLTISGLQAEDEADYYCSSYTSSSTRVFG

TGTKVTVLGQPKANPTVTLFPPSSEELQANKATLVCLISDFYPGAVTVAWK

ADGSPVKAGVETTKPSKQSNNKYAASSYLSLTPEQWKSHRSYSCQVTREGS

TVEKTVAPTECS;
```

The fusion peptide amino acid sequence of PD-L1 antibody 2 heavy chain/TGF-βRII extracellular domain (1-136) in FP17022 fusion protein:

```
                                    SEQ ID NO: 22
EVQLLESGGGLVQPGGSLRLSCAASGFTFSSYIMMWVRQAPGKGLEWVSSI

YPSGGITFYADTVKGRFTISRDNSKNTLYLQMNSLRAEDTAVYYCARIKLG

TVTTVDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFScSVMHEALHNHYTQKSLSLSPGAGGGGSGGGG

SGGGGSGGGGSGIPPHVQKSVNNDMIVTDNNGAVKFPQLCKFCDVRFSTCD

NQKSCMSNCSITSICEKPQEVCVAVWRKNDENITLETVCHDPKLPYHDFIL

EDAASPKCIMKEKKKPGETFFMCSCSSDECNDNIIFSEEYNTSNPD;
```

3. Test Process

CHO/PD-L1 cells (CS187108, Promega) were digested and resuspended in F-12 Nutrient Mixture (Ham) complete medium. The cell density was adjusted to $4 \times 10^5$/mL using complete medium according to the cell count results. The cell suspension was transferred to the loading tank, added to the 96-well plate at 100 μL/well using a multi-channel pipette, and incubated at 37° C., 5% $CO_2$ incubator for 20-24 h; The Jurkat/PD-1 (CS187102, Promega) cell suspension was prepared the next day, and the cells were resuspended according to the cell count results using assay medium, and the cell density was adjusted to $1.25 \times 10^6$/mL; The cell culture plates comprising CHO/PD-L1 cells were taken out from the incubator, 95 μL of the culture solution was taken out per well using a multi-channel pipette, and the gradient-diluted fusion protein, PD-L1 antibody and positive control (FP17022) were respectively added at 40 L/well. Then the Jurkat/PD-1 cell suspension was transferred to a loading tank, added to the cell culture plate at 40 μL/well, and incubated at 37° C., 5% $CO_2$ for 5-6 h. During the incubation with protein, the Bio-Glo™ Reagent was taken out and allowed to return to room temperature. Took out the cell culture plates and placed them at room temperature for 5-10 min. Then 40 μL Bio-Glo™ Reagent was added to each well, incubated in a safety cabinet for 5-10 min, and the chemi-luminescence signal value was read using a multi-function microplate reader.

4. Results

Figure 5:
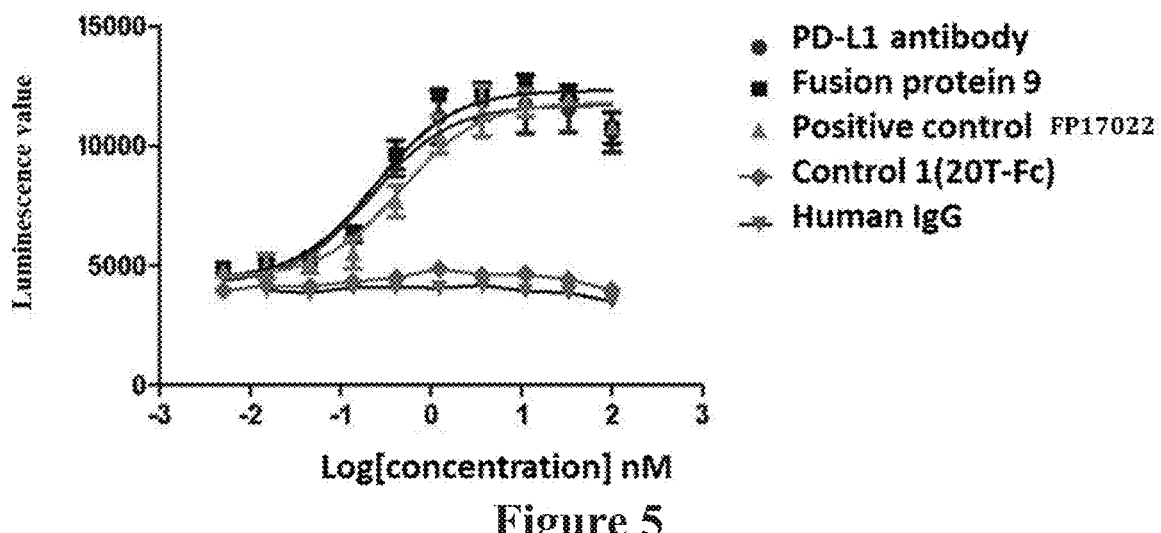
FIG. 5: Result showing the detection of PD-1/PD-L1 pathway blocking by fusion proteins in vitro.

As shown in FIG. 5, similarly to positive control molecule, the fusion protein 9 of the present disclosure was able to effectively block the binding of PD-1-expressing Jurkat cells to CHO/PD-L1 cells, and there was a drug concentration and dose-dependent effect. Fusion protein 15 has the same blocking ability as that of fusion protein 9.

Test Example 4: Binding Affinity and Kinetics Detection In Vitro by Biacore

The affinity of the test molecule to human or murine TGF-1 or human PD-L1 protein was determined by Biacore T200 (GE). The experimental procedure is described as follows:

A certain amount of PD-L1/TGF-β trap was captured with Protein A chip, and then the human or murine TGF-β1 (8915LC, CST) or human PD-L1 (Sino Biological) was flowed through the surface of the chip. The reaction signal was detected in real-time using Biacore to obtain the association and dissociation curves. The biochip was then washed and regenerated with glycine-hydrochloric acid (pH 1.5, GE). The buffer solution used in the experiment was HBS-EP Buffer (GE). The experimental data were fitted to (1:1) Langmuir model using BIAevaluation version 4.1 software (GE), and the affinity values were obtained and as shown in Table 3.

TABLE 3

| Affinity of fusion proteins of the present disclosure to TGF-β1 or human PD-L1 in virto | | | | |
|---|---|---|---|---|
| Fusion protein* | Affinity sample | ka (1/Ms) | kd (1/s) | KD (M) |
| Fusion protein 9 | Human TGF-β1 | 1.73E7 | 7.28E-4 | 4.22E-11 |
| Fusion protein 15 | | 2.69E7 | 6.08E-4 | 2.26E-11 |
| Fusion protein 9 | murine TGF-β1 | 4.33E7 | 1.33E-3 | 3.07E-11 |
| Fusion protein 15 | | 3.57E7 | 1.22E-3 | 3.42E-11 |
| Fusion protein 9 | human PD-L1 | 1.97E6 | 1.24E-4 | 6.31E-11 |
| Fusion protein 15 | | 2.00E6 | 1.24E-4 | 6.10E-11 |

*The form of fusion protein is shown in Table 2.

The fusion protein binding activity is shown in Table 3. The results indicate that the fusion protein 9 and fusion protein 15 of the present disclosure have extremely high affinity to human, murine TGF-β1 and human PD-L1.

Test Example 5: SMAD3 Reporter Gene Inhibition Assay

1. Test Purpose:

In this experiment, the Smad3 binding element (SBE) with luciferase reporter gene was expressed in HepG2 cells to study the inhibitory effect of PD-L1/TGF-β trap on TGF-β1-induced Smad3 activation, and the activity of PD-L1/TGF-β trap in vitro was evaluated according to IC50 value.

2. Test Sample: fusion protein 9, positive control (FP17022).

3. Test Process

HepG2 cells were cultured in MEM complete medium (GE, SH30243.01) comprising 10% FBS and sub-cultured every 3 days. On the first day of the experiment, 25,000 cells per well were inoculated to 96-well plates (Corning, 3903), and cultured at 37° C., 5% $CO_2$ for 24 hours. On the next day, the medium in the cell culture plates was discarded, and 100 ng of 3TP-Lux plasmid was transfected per well. The cells were further cultured at 37° C., 5% $CO_2$ for 24 hours. Six hours before the addition of the test sample, the complete medium in the 96-well plate was discarded, and 80 μL of incomplete medium (MEM+0.5% FBS) was added to each well. After 6 hours, 10 μL of human TGF-β1 (R&D, 240-B-010) solution prepared in incomplete medium (final concentration of 2 ng/mL) and 10 μL of the test sample (the final concentration is 500, 50, 5, 0.5, 0.05, 0.005, 0.0005 and 0 nM) were added, the human TGF-β1 solvent was used as a control, and the cells were cultured at 37° C., 5% $CO_2$ for another 18 h. Then, 100 μL of the prepared luciferase substrate ONE-Glo™ Luciferase Assay system (promega, E6110) was added to each well, and incubated at room temperature for 10 minutes in dark, and then the luminescent signal value was read using a Victor 3 multi-plate reader (Perkin Elmer). The IC50 value of the test sample was obtained by calculating using the data software Graphpad Prism 5.0.

Figure 6:
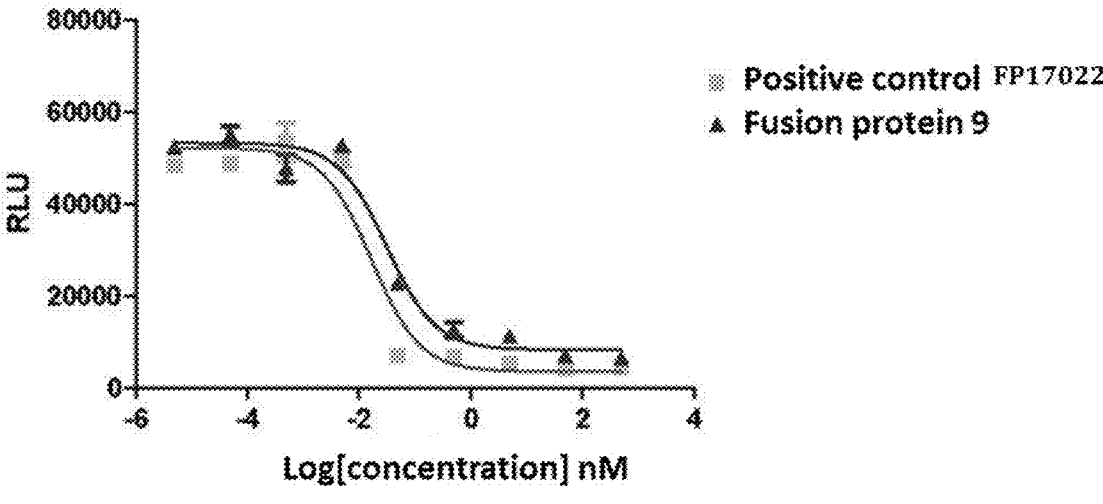
FIG. 6: Fusion proteins inhibit TGFβ-induced activity of pSMAD3 reporter in a dose-dependent manner.

FIG. 6 showed that fusion protein 9 inhibited TGFβ-induced pSMAD3 reporter activity in a dose-dependent manner, and had efficacy and $IC_{50}$ (concentration required to inhibit 50% of maximum activity) comparable to that of positive control FP17022. The test results of the PD-L1 antibody showed that it had no inhibitory effect ($IC_{50}$>500 nM).

Test Example 6: In Vitro Detection of IFNγ Secretion by PBMC Due to Tuberculin (TB) Stimulation 1. Test Purpose To investigate the activation of T lymphocytes by PD-L1/TGF-β trap, human peripheral blood mononuclear cells (PBMC) were collected and purified, and were stimulated in vitro with tuberculin (TB) for 5 days to detect the secretion level of IFNγ cytokine.

2. Test Sample

① Human IgG;
    ② PD-L1 antibody;
    ③ Fusion protein 9;
    ④ Control 1 (20T-Fc): ECD (20-136)-Fc;
    ⑤ PD-L1 antibody+control 1 (20T-Fc).

3. Test Process

20 μL tuberculin was added into freshly isolated and purified PBMCs, 15 mL, about 3×10^7, and cultured in an incubator for 5 days at 37° C., 5% $CO_2$. On day 6, the cultured cells were collected and centrifuged, washed once with PBS and resuspended in fresh medium with the density adjusted to $1×10^6$ cell/ml, 90 μl of resuspended cells were added into the 96-well plate. 10 μL/well of different concentrations of antibodies were separately added to corresponding wells of the above 96-well cell culture plate, 10 μl PBS was added in the control and blank group, respectively. Then, the cell culture plate was incubated in the incubator for three days at 37° C., 5% $CO_2$. The cell culture plate was taken out, and the supernatant was taken from each well after centrifugation (4000 rpm, 10 min). After 10-fold dilution, the secretion of IFN-γ was detected by ELISA (human IFN-γ detection kit, NEOBIOSCIENCE, EHC 102g.96), according to the reagent instructions for specific operations. As shown in Table 4, all the PD-L1/TGF-β trap fusion protein samples were able to enhance the secretion of cytokine IFN-γ by the activated T lymphocytes, and there was a drug concentration dose effect.

TABLE 4

| The secretion result of cytokine IFN-γ | | | | |
|---|---|---|---|---|
| Antibody | EC50 (nM) | Maximum secretion of IFNγ (pg/ml) | Minimal secretion of IFNγ (pg/ml) | Fold (secretion of IFNγ) |
| PD-L1 antibody | 0.05 | 2684 | 737 | 3.6 |
| Fusion protein 9 | 0.12 | 3422 | 638 | 5.4 |
| Control 1(20T-Fc) | >50 | 780 | 490 | 1.6 |
| PD-L1 antibody + control 1 | 0.054 | 2879 | 746 | 3.9 |
| Human IgG | >50 | 375 | 298 | 1.2 |
| Blank control | / | 536 | 536 | 1 |

4. Result

Figure 7:
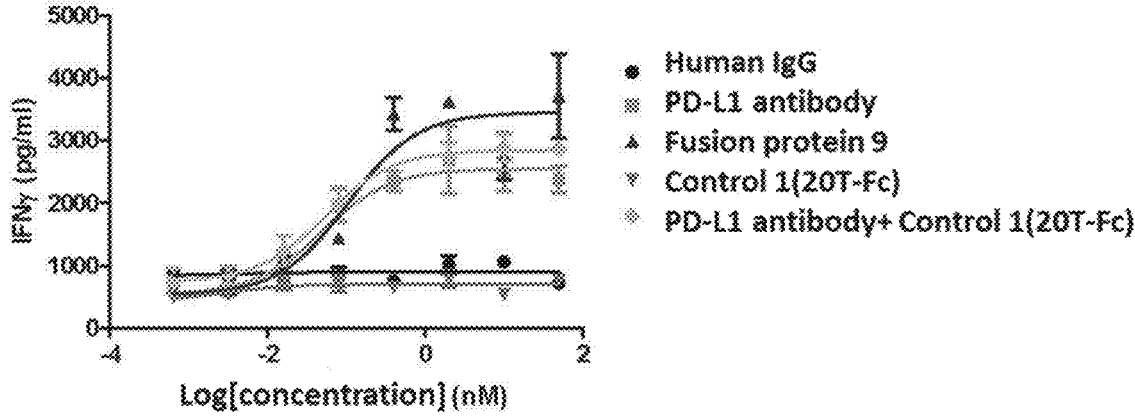
FIG. 7: All samples of fusion proteins enhance the secretion of the cytokine IFN-γ by activated T lymphocytes.

As shown in FIG. 7 and Table 4, the fusion protein 9 was able to enhance the activated T lymphocyte to secrete cytokine IFN-γ in dose-dependent manner, and had a stronger activation effect than that of the PD-L1 antibody and 20T-FC.

Test Example 7: Pharmacokinetic Evaluation

Three SD rats, female, were purchased from Jie Si Jie Laboratory Animal Co., Ltd. and maintained in 12/12-hour light-dark cycle (the temperature was 24±3° C., the relative humidity was 50-60%), the rats were free access to water and diet. On the day of the experiment, SD rats were injected with fusion protein in the tail vein at a dose of 6 mg/kg and an injection volume of 5 ml/kg.

Blood was collected at time point: 15 min, 7 h (on the first day), 24 h ($2^{nd}$ day), $3^{rd}$ day, $4^{th}$ day, $6^{th}$ day, $8^{th}$ day, $10^{th}$ day, and $15^{th}$ day after administration, 200 μl blood (equivalent to 100 μl serum) was taken from the fundus vein of the rat. The blood sample was placed at room temperature for 30 min to allow agglutination, and then centrifuged at 10000 g for 10 minutes at 4° C. The supernatant were taken and stored at −80° C. immediately. The concentration of the fusion protein in the serum was measured by ELISA.

The measure process is described as follows:

a. 96-well plates were coated with 100 μl/well of human PD-L1-His at a concentration of 2 μg/ml, overnight at 4° C.

b. Washing 4 times with 250 μl of 1×PBST, 250 μl of 5% milk PBS was added for blocking at 37° C. for 3 hours.

c. Washing 4 times with 250 μl of 1×PBST, 100 μl of the gradient-diluted serum sample was added, and incubated at 37° C. for 1 hour, with fusion protein 9 served as positive control.

d. Washing 5 times with 250 µl 1×PBST.

e. 100 µl/well of biotinylated anti-human TGF-βRII antibody (R&D) was added, and incubated for 1 hour at 37° C.

f. Washing 5 times with 250 µl 1×PBST.

g. 100 µl/well of TMB was added, incubated for 10 minutes at room temperature, and the reaction was stopped by adding 100 µl of 1 M $H_2SO_4$.

h. The absorbance at 450 nm was measured on a microplate reader, and the data was analyzed by Graphpad Prism 5.

TABLE 5

| $T\frac{1}{2}$ of fusion protein in SD rat | | |
|---|---|---|
| Test drug | Administration mode | $T\frac{1}{2}$ (Mean ± SD, h) |
| Fusion protein 9 | IV (6 mg/kg) | 236 ± 10 |

The results of PK analysis indicated that the half-life of the fusion protein 9 of the present disclosure in rats was about 236 h (9.8 days), see table 5.

Test Example 8: Effect of PD-L1/TGF-β Trap on Murine Subcutaneous Xenograft of Human Breast Cancer MDA-MB-231

The murine strain used in this experiment was a NOD/SCID female mouse (Cavens). The human peripheral blood mononuclear cells used in the experiment were extracted from freshly collected blood, and the extraction method was as follows: The heparin anti-coagulated venous blood was mixed with the same volume of PBS containing 2% FBS, and after mixing, 25 ml of the diluted blood was slowly added to a centrifuge tube containing 15 ml of lymphocyte separation solution, and centrifuged at 1200 g for 10 minutes at room temperature. The lymphocyte layer was pipetted to another centrifuge tube; cells were washed by PBS and centrifuged at 300 g for 8 minutes at room temperature. After repeated once, the cells were re-suspended in RPMI-1640 medium containing 10% FBS, and the cells were added to a 6-well plate pre-coated with CD3 antibody (OKT3, 40 ng/ml) at $2\times10^6$ cells/well (2 ml), and then placed in a 37° C. incubator for 4 days.

Test Sample:
- (1) blank control: PBS;
- (2) fusion protein 9: 4.8 mpk;
- (3) fusion protein 9: 24 mpk;
- (4) PD-L1 antibody: 4 mpk;
- (5) PD-L1 antibody: 20 mpk;
- (6) PD-L1 antibody 4 mpk+control 1 (20T-Fc) 2.14 mpk;
- (7) Control 1 (20T-Fc): 2.14 mpk.

MDA-MB-231 cells were re-suspended in serum-free RPMI-1640 medium, and mixed with an equal volume of Matrigel, 100 µl ($2.3\times10^6$) was inoculated subcutaneously into the right flank of NOD/SCID mice. 11 days later, animals bearing oversized or undersized tumor were excluded, mice were randomized into groups, with 9 animals in each group. $5\times10^5$ stimulated PBMCs (60 µl) were injected into the tumor tissues, and the remaining PBMCs were further cultivated without stimulation. One week later, $5\times10^6$ PBMCs (100 µl) were intraperitoneally injected into tumor-bearing mice, as the first round of injection. Throughout the experimental period, 2 and a half-round, a total of 5 PBMC injections were provided. On the day of the first intratumoral injection, intraperitoneal administration was performed, three times per week for a total of 14 administrations. The administration regimen was shown in Table 6. The tumor volume and body weight were measured twice a week. The experimental results are shown in Table 7. At the end of the experiment, the tumor-bearing mice were euthanized and the tumor was removed and weighed.

TABLE 6

| Test grouping and administration | |
|---|---|
| Group | Administration Dose |
| (1) Blank control: PBS | 0 |
| (2) Fusion protein 9- 4.8 mpk | 4.8 mg/kg |
| (3) Fusion protein 9- 24 mpk | 24 mg/kg |
| (4) PD-L1antibody- 4 mpk | 4 mg/kg |
| (5) PD-L1 antibody - 20 mpk | 20 mg/kg |
| (6) PD-L1 antibody- 4 mpk + control 1- 2.14 mpk | 4 mg/kg + 2.14 mg/kg |
| (7) Control 1- 2.14 mpk | 2.14 mg/kg |

TABLE 7

| | Day 0 | Day 25 | | Day 32 | | Day 33 | |
|---|---|---|---|---|---|---|---|
| Effect of fusion protein 9 on murine subcutaneous xenograft of MDA-MB-231 | | | | | | | |
| Group | Mean ± SEM (V mm³) | Mean ± SEM (V mm³) | % TGI | Mean ± SEM (V mm³) | % TGI | Mean ± SEM (TW g) | P (vs PBS) (TW) |
| (1) Blank control: PBS | 62.5 ± 2.9 | 623.4 ± 43.3 | — | 941.1 ± 54.9 | — | 0.859 ± 0.063 | — |
| (2) Fusion protein 9- 4.8 mpk | 62.6 ± 3.5 | 414.6 ± 17.1*** | 37.24% | 618.9 ± 28.7*** | 36.68% | 0.454 ± 0.025*** | 2.06E–05 |
| (3) Fusion protein 9- 24 mpk | 62.7 ± 3.3 | 329.8 ± 22.5*** | 52.38% | 495.3 ± 42.6*** | 50.76% | 0.367 ± 0.026*** | 2.20E–06 |
| (4) PD-L1 antibody - 4 mpk | 63.1 ± 3.5 | 454.4 ± 40.8* | 30.24% | 722.8 ± 65.8* | 24.91% | 0.592 ± 0.052** | 0.0050 |
| (5) PD-L1 antibody - 20 mpk | 62.6 ± 3.3 | 466.4 ± 17.2** | 28.01% | 741.8 ± 32.9** | 22.70% | 0.650 ± 0.033** | 0.0100 |

TABLE 7-continued

| | Day 0 | Day 25 | | Day 32 | | Day 33 | |
|---|---|---|---|---|---|---|---|
| Group | Mean ± SEM (V mm³) | Mean ± SEM (V mm³) | % TGI | Mean ± SEM (V mm³) | % TGI | Mean ± SEM (TW g) | P (vs PBS) (TW) |
| ⑥ PD-L1 antibody - 4 mpk + control 1- 2.14 mpk | 62.6 ± 3.3 | 447.5 ± 29.6** | 31.38% | 669.2 ± 45.3** | 30.96% | 0.566 ± 0.039** | 0.0012 |
| ⑦ Control 1 - 2.14 mpk | 60.7 ± 3.3 | 601.5 ± 30.9 | 3.58% | 861.7 ± 34.2 | 8.83% | 0.652 ± 0.041* | 0.0178 |

*Effect of fusion protein 9 on murine subcutaneous xenograft of MDA-MB-231*

Day 0: time for the first administration;
*$p < 0.05$
**$p < 0.01$
***$p < 0.001$, when compared with PBS by Student's t test.

Figure 8:
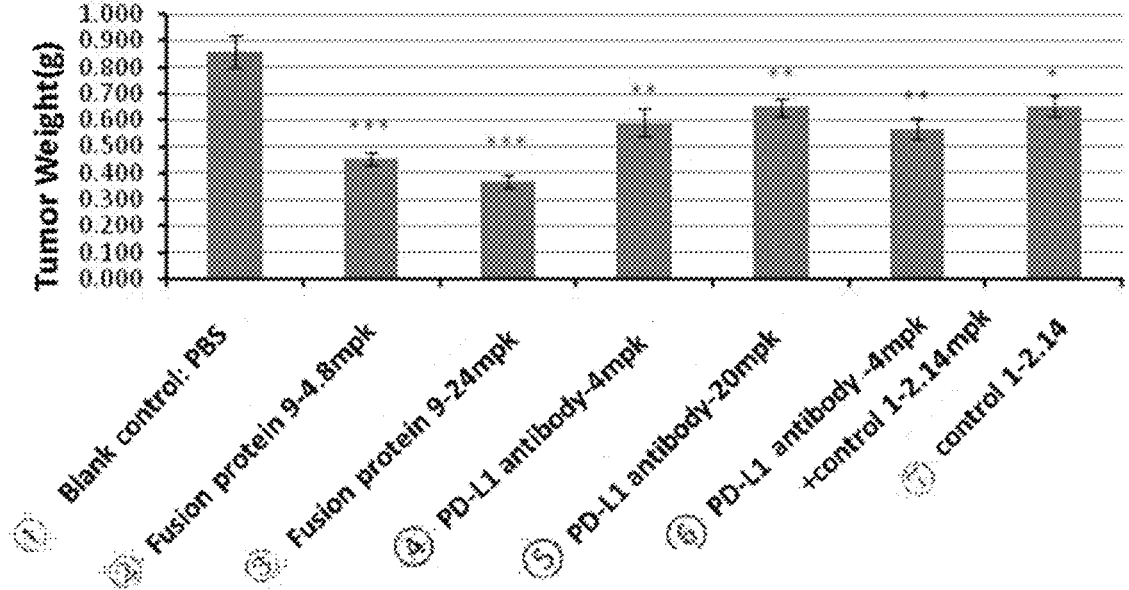
FIG. 8: Effect of fusion proteins on tumor weight of tumor-bearing mice.

The results are shown in FIG. 8, antibody fusion protein 9 (4.8 mg/kg, 24 mg/kg) can significantly inhibit the growth of murine subcutaneous xenograft of human breast cancer MDA-MB-231. There was a dose-dependent relationship between high and low doses, and it was superior to reference drug PD-L1 antibody (4 mg/kg, 20 mg/kg), TGF-βRII control molecule 20T-FC (2.14 mg/kg) and the combination group (PD-L1 antibody—4 mg/kg+20 T-FC-2.14 mg/kg) at equivalent molar dose, respectively. Each dose of fusion protein 9 maintained a desired anti-tumor effect since the $14^{th}$ day after administration; when compared with PD-L1 antibody-20 mpk, fusion protein 9 at high dose had obvious advantage ($p < 0.05$). On the $25^{th}$ days after administration, the anti-tumor effect of each antibody reached an optimum level. The anti-tumor rate of the low and high dose of fusion protein 9 and PDL-1 antibody and the combination group was 37.24%, 52.38%, 30.24%, 28.01%, and 31.38%, respectively. On the $32^{th}$ days after administration, the antitumor effect of fusion protein 9 was still very significant. The % TGI of the low and high dose group was 36.68% and 50.76%, respectively, and the tumor volume was statistically different, when compared with the control group ($p < 0.05$).

Test Example 9: Physical Stability of PD-L1/TGF-β Trap

This test example was used to detect the stability of fusion protein 9 and fusion protein 15.

DSC (Differential scanning calorimetry) was used to detect the thermal stability of different antibodies, and the stability in different buffer systems was compared. Buffer systems comprise such as 10 mM acetate/135 mM NaCl (pH 5.5) and 10 mM acetate/9% trehalose (pH 5.5).

The sample was dissolved in the corresponding buffers, and the concentration was controlled at about 50 mg/ml. The detection was performed by MicroCal* VP-Capillary DSC (Malvern). Prior to test, each sample and blank buffer were degassed for 1 to 2 min using a vacuum degassing device. Each well of the plate was added with 400 μl sample or blank buffer (the loading quantity was 300 μl). Finally, two pairs of well-plates were added with 14% Decon 90 and ddH₂O, respectively, and were ready to wash. The sample was loaded on the plate, and then the plate was sealed with a plastic cover. Scanning began with a temperature at 25° C. and ended at 100° C., and the scanning rate is 60° C./h. The results are shown in table 8, indicating that both fusion protein 9 and fusion protein 15 show good thermal stability in these two test systems.

TABLE 8

| | | Tm-onset (° C.) | TM (° C.) |
|---|---|---|---|
| Sample | Buffer | | |
| Fusion protein 9 | 10 mM acetate/135 mM NaCl | 57.99 | 66.33 |
| | 10 mM acetate/9% trehalose | 58.64 | 67.83 |
| Fusion protein 15 | 10 mM acetate/135 mM NaCl | 57.33 | 66.17 |
| | 10 mM acetate/9% trehalose | 57.41 | 67.44 |

*Thermal stability test*

The periodic stability at certain concentration was investigated by monitoring purity via SEC-HPLC, exemplary conditions, for example, the concentration of the sample was controlled at about 50 mg/ml, in 10 mM acetate/135 mM NaCl (pH5.5), and the stability was compared under the conditions such as 5 cycles of freezing and thawing at −80° C. versus after storage at 40° C. for one month. Xbridge protein BEH SEC 200A (Waters) HPLC column was used for detection. The results are shown in table 9 as follows, these two fusion protein showed good stability.

TABLE 9

| | fusion protein 9(Δ%) | fusion protein 15(Δ%) |
|---|---|---|
| 40° C. | 3.39% | 1.8% |
| −80° C. freeze-thaw | 1.44% | 1.39% |

*stability*

Note:
Δ% indicates the rate of change.

Test Example 10: Chemical Stability of Fusion Protein

Deamidation is a common chemical modification which will influence the stability of antibody in later stage, especially it is generally chosen to avoid or to reduce the highly deamidated modification of some amino acids in the CDR regions as much as possible via mutation. 1600 μg antibody to be tested was dissolved in 200 μl 10 mM acetate/135 mM NaCl (pH5.5), and placed in 40° C. incubator. Samples were taken on day 0, 14 and 28 for enzymatic hydrolysis assay. 100 μg of each sample taken at different time points was dissolved in 100 μl 0.2 M His-HCl, 8 M Gua-HCl solution, pH 6.0; 3 μl 0.1 g/mL DTT was added, and then the sample was incubated in 50° C. water bath for 1 hour. Then the sample was ultrafiltrated twice with 0.02M His-HCl (pH 6.0), and digested overnight at 37° C. in water bath by adding 3 μL 0.25 mg/mL trypsin. The deamidation modification was examined using an Agilent 6530 Q-TOF LC-MS, and the results are shown in Table 10 below.

TABLE 10

| Deamidation modification | | | | | |
| --- | --- | --- | --- | --- | --- |
| Sample | Heavy chain | Modification site | Day 0 | Day 14 | Day 28 |
| Fusion protein 9 | Heavy chain | N314 | 2.38% | 2.28% | 2.45% |
| | | N324 | 0.20% | 3.60% | 7.88% |
| Fusion protein 15 | Heavy chain | N314 | 2.87% | 2.86% | 2.87% |
| | | N324 | 0.00% | 3.61% | 7.93% |

Note:
N represents the detectable modified asparagine, and the number represents the position in the light chain or heavy chain from N-terminus. The percent content represents the ratio of deamidation modification detected by LC-MS to the signal of all peptides at that site.

The results of mass spectrometry showed that the two fusion proteins don't have obvious deamidation modification sites, suggesting that the fusion proteins have good chemical stability.

Preparation Example

Exemplary Preparation Processes for Fusion Protein Pharmaceutical Composition (Preparation)

The first step: a certain amount of stock solution of purified TGF-β receptor fusion protein was taken, and solvent replacement (preferably by ultrafiltration) was performed using a protein-free buffer (such as 10 mM, pH 6.2 citric acid-sodium citrate buffer) by passing through an ultrafiltration membrane for at least 6-fold volume, then the protein was concentrated to about 70 mg/mL. A certain volume of sucrose stock solution was added and mixed to achieve a final sucrose concentration of 80 mg/mL. A certain volume of Tween-80 stock solution was added and mixed to achieve a final Tween-80 concentration of 0.4 mg/mL. 10 mM pH 6.2 citrate buffer was added to reach a specified volume so as to obtain a concentration of 50 mg/mL protein (other preparations to be tested or stable preparations were prepared according to similar steps).

After having been filtrated, the product was sampled for sterility test due to medium-control purpose. The stock solution passed through a 0.22 μm PVDF filter and the filtrate was collected.

The second step: the filling volume was adjusted to 6.3 ml, the filtrate was loaded into a 6 ml vial, which was then capped with a stopper, and samples were taken at the beginning of, in the middle of, and at the end of filling in order to detect the difference in filling volume, due to medium-control purpose.

The third step: the capping machine was started, aluminum caps were capped.

The fourth step: visual inspection was performed to confirm that the product has no defects such as inaccurate loading. Labels were printed and labelled on vials: carton labels were printed, cartons were folded, loaded with vials, and labelled.

Preparation Example 1. Screening of pH Value for Preparation Buffer System of TGF-β Receptor Fusion Protein TGF-β receptor fusion protein (fusion protein 9) preparations were prepared using the following buffers, with a protein concentration of 50 mg/ml:

1) 10 mM histidine-acetic acid, pH 5.0;
2) 10 mM histidine-acetic acid, pH 6.0;
3) 10 mM histidine-acetic acid, pH 6.5;
4) 10 mM sodium dihydrogen phosphate-disodium hydrogen phosphate, pH 7.0;
5) 10 mM sodium dihydrogen phosphate-disodium hydrogen phosphate, pH 7.5.

Each preparation was filtrated, and added at 1.2 mL/vial into a 2 mL injection vial made of neutral borosilicate glass. The injection vial was provided with a stopper, capped and sealed. The samples were taken and subjected to a high temperature of 40° C. and shaking experiments.

The experimental results are shown in Table 11. The results show that TGF-β receptor fusion proteins have better stability at pH 6.0-6.5.

TABLE 11

| | | | Screening results of forced degradation experiment | | |
| --- | --- | --- | --- | --- | --- |
| | | | | SEC (%) | |
| No. | Time point | Appearance | aggregate | monomer | fragment |
| 1 | T0 | strong opalescence | 2.0 | 97.1 | 1.0 |
| | with shaking D 7 | turbid | 3.5 | 94.8 | 1.7 |
| | 40° C. M 2 | clear and colorless | 8.1 | 87.1 | 4.7 |
| 2 | T0 | light blue opalescence | 2.7 | 97.0 | 0.3 |
| | with shaking D 7 | turbid | 3.0 | 96.2 | 0.9 |
| | 40° C. M 2 | clear and colorless | 5.9 | 91.1 | 3.0 |
| 3 | T0 | clear and colorless | 2.7 | 96.9 | 0.3 |
| | with shaking D 7 | large amount of flocculent precipitate | 3.0 | 95.7 | 1.3 |
| | 40° C. M 2 | clear and colorless | 5.0 | 91.7 | 3.3 |
| 4 | T0 | colorless and fine particles | 3.1 | 96.5 | 0.5 |
| | with shaking D 7 | large amount of flocculent precipitate | 3.6 | 95.3 | 1.2 |
| | 40° C. M 2 | clear and colorless | 4.5 | 71.5 | 23.9 |
| 5 | T0 | colorless and fine particles | 3.2 | 96.5 | 0.4 |
| | with shaking D 7 | large amount of flocculent precipitate | 3.7 | 95.0 | 1.3 |
| | 40° C. M 2 | clear and colorless | 4.9 | 60.8 | 34.3 |

Note:
The shaking condition was: D 1: 130 rpm, D 2: 200 rpm, D 3-D 7: 300 rpm; D means day, T means time, and M means month.

Preparation Example 2. Screening of Buffer System
for TGF-β Receptor Fusion Protein Preparations TGF-β receptor fusion protein (fusion protein 9) preparations were prepared using the following buffers, with a protein concentration of 50 mg/ml:
  1) 10 mM succinic acid-sodium succinate, pH 6.0;
  2) 10 mM citric acid-sodium citrate, pH 6.0;
  3) 10 mM citric acid-sodium citrate, pH 6.5;
  4) 10 mM sodium dihydrogen phosphate-disodium hydrogen phosphate, pH 6.5;
  5) 10 mM histidine-hydrochloride, pH 6.5.

Each preparation was filtrated, and added at 1.2 mL/vial into a 2 mL injection vial of neutral borosilicate glass. The injection vial was provided with a stopper, capped and sealed. The samples were taken for shaking (at 25° C., 300 rpm) experiment. The experimental results are shown in Table 12. The results show that a large amount of small particles were observed in the group of sodium dihydrogen phosphate-disodium hydrogen phosphate on the 6th day under shaking, and the aggregates reached 1.8% detected by SEC. However, only tiny particles were occasionally observed in other groups. It can be seen that the stability of TGF-β receptor fusion protein in citric acid, histidine and succinate buffer systems is better than that in phosphate buffer systems.

Preparation Example 3. Further Screening of Buffer
System for TGF-β Receptor Fusion Protein
Preparation A buffer of pH 6.2 comprising 10 mM histidine-hydrochloride or 10 mM citric acid-sodium citrate was used to prepare a preparation comprising 80 mg/ml sucrose, 0.4 mg/ml polysorbate 80, TGF-β receptor fusion protein (fusion protein 9) at a concentration of 50 mg/ml.

Each preparation was filtrated, and added at 1.2 mL/vial into a 2 mL injection vial made of neutral borosilicate glass. The injection vial was provided with a stopper, capped and sealed. The samples were stored at 25° C. for stability analysis, 6-month SEC or non-reducing CE-SDS detection.

The experimental results are shown in Table 13. The results show that the citric acid-sodium citrate system is better than the histidine-hydrochloride system (M6 SEC aggregate: 1.8% v.s. 2.2%; non-reducing CE-SDS: 94.5% v.s. 92.2%); Thus, the citric acid system can be selected as the buffer system for TGF-β receptor fusion protein.

TABLE 12

| | | screening experiment results for buffer system and pH value | | | |
| --- | --- | --- | --- | --- | --- |
| | | | | SEC (%) | |
| No. | Time point | Appearance | aggregate | monomer | fragment |
| 1 | D 0 | clear and colorless | 1.6 | 98.1 | 0.3 |
| | with shaking D 6 | tiny particles occasionally | 1.7 | 97.7 | 0.6 |
| 2 | D 0 | clear and colorless | 1.5 | 98.0 | 0.5 |
| | with shaking D 6 | tiny particles occasionally | 1.5 | 97.8 | 0.7 |
| 3 | D 0 | clear and colorless | 1.6 | 98.0 | 0.4 |
| | with shaking D 6 | tiny particles occasionally | 1.7 | 97.7 | 0.6 |
| 4 | D 0 | clear and colorless | 1.6 | 98.0 | 0.4 |
| | with shaking D 6 | large amount of tiny particles | 1.8 | 97.6 | 0.7 |
| 5 | D 0 | clear and colorless | 1.5 | 98.0 | 0.5 |
| | with shaking D 6 | tiny particles occasionally | 1.6 | 97.8 | 0.7 |

Note:

D represents days.

TABLE 13

| Buffer system | Time | Appearance | SEC (%) | | | Non-reducing CE-SDS (%) |
|---|---|---|---|---|---|---|
| | | | aggregate | monomer | fragment | |
| citrate | T0 | clear | 1.6 | 97.6 | 0.7 | 91.2 |
| buffer system | D 24 | clear | 1.6 | 97.7 | 0.7 | 90.4 |
| | M 2 | clear | 1.7 | 97.5 | 0.8 | N/A |
| | M 3 | clear | 1.8 | 97.9 | 0.3 | 96.2 |
| | M 6 | large amount of cloudy particles | 1.8 | 97.9 | 0.4 | 94.5 |
| histidine salt | T0 | clear | 1.5 | 97.7 | 0.8 | 91.3 |
| buffer system | D 24 | clear | 1.6 | 97.4 | 1.1 | 90.4 |
| | M 2 | clear | 1.7 | 97.5 | 0.8 | N/A |
| | M 3 | clear | 1.8 | 97.7 | 0.5 | 95.4 |
| | M 6 | large amount of cloudy particles | 2.2 | 97.3 | 0.5 | 92.2 |

Accelerated stability test results for buffer system screening at 25° C.

Note:
T means time; D means day; M means month.

Preparation Example 4. Screening of Stabilizers for TGF-β Receptor Fusion Protein Preparations TGF-β receptor fusion protein (fusion protein 9) preparations were prepared using the following buffers of different saccharides, with a protein concentration of 50 mg/ml:
1) 10 mM citric acid-sodium citrate, 80 mg/ml sucrose, pH 6.2;
2) 10 mM citric acid-sodium citrate, 80 mg/ml α,α-trehalose dihydrate, pH 6.2.

Each preparation was filtrated, and added at 1.2 mL/vial into a 2 mL injection vial made of neutral borosilicate glass. The injection vial was provided with a stopper, capped and sealed. The samples were taken for long-term storage experiments at 25° C. room temperature and at 2-8° C. low temperature.

The experimental results are shown in Table 14. The results show that sucrose and trehalose have similar effects on the stability of TGF-β receptor fusion protein (fusion protein 9). Sucrose was selected as the stabilizer of TGF-β receptor fusion protein (fusion protein 9). When the sucrose concentration is 80 mg/ml, the osmotic pressure is about 300 mosm/kg which is close to being isotonic, therefore the sucrose concentration can be 80 mg/ml.

Table 14. Results of Screening Experiments for Types of Saccharide

TABLE 14

Results of screening experiments for types of saccharide

| No. | Time point | Appearance | SEC (%) | | | Non-reducing CE-SDS (%) |
|---|---|---|---|---|---|---|
| | | | aggregate | monomer | fragment | |
| 1 | T0 | clear and colorless | 1.6 | 97.6 | 0.7 | 91.2 |
| | 25° C. M 6 | large amount of cloudy particles | 1.8 | 97.9 | 0.4 | 94.5 |
| | 2-8° C. M 6 | clear and colorless | 1.7 | 98.1 | 0.1 | 96.8 |
| 2 | T0 | clear | 1.6 | 97.7 | 0.7 | 91.6 |
| | 25° C. M 6 | significant cloudy particles | 1.9 | 97.8 | 0.3 | 94.1 |
| | 2-8° C. M 6 | clear and colorless | 1.8 | 97.8 | 0.4 | 97.5 |

Note:

T means time, and M means month.

Preparation Example 5. Screening of Surfactants
for TGF-β Receptor Fusion Protein Preparations TGF-β receptor fusion protein (fusion protein 9) preparations were prepared using the following buffers of different types surfactants at different concentrations, with a protein concentration of 50 mg/ml:

1) 10 mM histidine-hydrochloride, 0.1 mg/ml polysorbate 20, pH 6.2;

2) 10 mM histidine-hydrochloride, 0.2 mg/ml polysorbate 20, pH 6.2;

3) 10 mM histidine-hydrochloride, 0.4 mg/ml polysorbate 20, pH 6.2;

4) 10 mM histidine-hydrochloride, 0.6 mg/ml polysorbate 20, pH 6.2;

5) 10 mM histidine-hydrochloride, 0.8 mg/ml polysorbate 20, pH 6.2;

6) 10 mM histidine-hydrochloride, 0.1 mg/ml polysorbate 80, pH 6.2;

7) 10 mM histidine-hydrochloride, 0.2 mg/ml polysorbate 80, pH 6.2;

8) 10 mM histidine-hydrochloride, 0.4 mg/ml polysorbate 80, pH 6.2;

9) 10 mM histidine-hydrochloride, 0.6 mg/ml polysorbate 80, pH 6.2;

10) 10 mM histidine-hydrochloride, 0.8 mg/ml polysorbate 80, pH 6.2.

Each preparation was filtrated, 0.5 mL of preparation was injected into 50 mL saline injection or into 5% glucose injection solution, to reach a protein concentration of 0.5 mg/mL after dilution. The sample stability after dilution was observed. The results of the experiment are shown in Table 15. The results show that when the concentration of polysorbate 20 in the preparation reached more than 0.2 mg/ml, the insoluble particles decreased significantly after dilution; as for polysorbate 80, the insoluble particles produced due to sodium chloride dilution decreased along with the increase of polysorbate 80 concentration. When polysorbate 80 reached 0.4 mg/ml or more, particles larger than 10 μm was reduced to less than 10 particles/ml.

42

TABLE 15

| results of polysorbate screening - dilution and shaking experiment | | | | | | |
|---|---|---|---|---|---|---|
| | Insoluble particles after dilution (particles/ml) | | | | | |
| | 0.9% NaCl | | | 5% Glucose | | |
| No. | 2 μm | 10 μm | 25 μm | 2 μm | 10 μm | 25 μm |
| 1 | 1454 | 18 | 0 | 318 | 10 | 0 |
| 2 | 48 | 1 | 0 | 104 | 2 | 0 |
| 3 | 65 | 2 | 0 | 177 | 3 | 0 |
| 4 | 26 | 1 | 0 | 102 | 1 | 0 |
| 5 | 112 | 3 | 0 | 82 | 2 | 0 |
| 6 | 568 | 36 | 1 | 46 | 1 | 0 |
| 7 | 668 | 14 | 0 | 30 | 1 | 0 |
| 8 | 135 | 3 | 0 | 92 | 4 | 0 |
| 9 | 623 | 8 | 0 | 30 | 1 | 0 |
| 10 | 113 | 2 | 0 | 97 | 6 | 0 |

Preparation Example 6. Further Screening of
Surfactants for TGF-β Receptor Fusion Protein
Preparations TGF-β receptor fusion protein (fusion protein 9) preparations were prepared using the following buffers of different types surfactants, with a protein concentration of 50 mg/ml:

1) 10 mM citric acid-sodium citrate, 0.4 mg/ml polysorbate 80, pH 6.2;

2) 10 mM citric acid-sodium citrate, 0.6 mg/ml polysorbate 20, pH 6.2.

Each preparation was filtrated, and added at 1.2 mL/vial into a 2 mL injection vial made of neutral borosilicate glass. The injection vial was provided with a stopper, capped and sealed. The samples were taken for long-term storage experiments at 2-8° C. low temperature.

The experimental results are shown in Table 16. The results indicate that polysorbate 80 has a better stability effect on TGF-β receptor fusion protein (fusion protein 9). Therefore, polysorbate 80 was selected as surfactant for TGF-β receptor fusion protein (fusion protein 9).

TABLE 16

| Results of long-term stability experiment at 2-8° C. for screening Polysorbate | | | | | | |
|---|---|---|---|---|---|---|
| | | | SEC (%) | | | Non-reducing CE-SD |
| No. | Time point | Appearance | aggregate | monomer | fragment | (%) |
| 1 | T0 | clear and colorless | 1.6 | 97.6 | 0.7 | 91.2 |
| | D 45 | clear and colorless | 1.7 | 97.4 | 1.0 | N/A |
| | M 3 | clear and colorless | 1.8 | 98.0 | 0.3 | 97.4 |
| | M 6 | clear and colorless | 1.7 | 98.1 | 0.1 | 96.8 |
| 2 | T0 | clear and colorless | 1.6 | 97.8 | 0.6 | 91.7 |
| | D 45 | large amount of particles | 1.7 | 97.5 | 0.8 | N/A |
| | M 3 | large amount of particles | 1.8 | 97.9 | 0.3 | 97.5 |
| | M 6 | large amount of particles and turbid | 1.7 | 97.8 | 0.4 | 96.7 |

Note:
T means time, D means day, and M means month.

Preparation Example 7. Filter Membrane
Compatibility Test for TGF-β Receptor Fusion
Protein Preparations TGF-β receptor fusion protein (fusion protein 9) was
formulated at 50 mg/ml in 10 mM citric acid-sodium citrate
buffer, 80 mg/ml sucrose, 0.4 mg/ml polysorbate 80, pH 6.2.
The preparations passed through a 0.22 μm PES filter
membrane and a PVDF filter membrane, respectively, and
samples were taken at the beginning of, in the middle of and
at the end of testing.

The experimental results are shown in Table 17. The
protein content, appearance and purity analysis show that
TGF-β receptor fusion protein (fusion protein 9) was stable
during the contact with the filter membrane, and the prepa-
ration was compatible with both PES and PVDF filter
membranes.

TABLE 17

| Test results of compatibility with filter membranes | | | | | |
|---|---|---|---|---|---|
| | Concentration of protein | SEC % | | | Non-reducing CE-SDS | Polysorbate content |
| Filter membrane | mg/ml | aggregate | monomer | fragment | % | mg/ml |
| T0 | 50.8 | 0.8 | 98.9 | 0.3 | 98.1 | 0.46 |
| PES, primary filtrate | 51.4 | 0.9 | 98.9 | 0.2 | 98.0 | 0.46 |
| PES, medium filtrate | 49.8 | 0.9 | 98.9 | 0.3 | 98.0 | 0.46 |
| PES, final filtrate | 50.0 | 0.9 | 98.9 | 0.2 | 98.0 | 0.46 |
| PVDF, primary filtrate | 49.6 | 0.9 | 98.7 | 0.4 | 97.9 | 0.46 |
| PVDF, medium filtrate | 50.2 | 0.9 | 98.8 | 0.3 | 98.0 | 0.46 |
| PVDF, final filtrate | 50.0 | 0.9 | 98.8 | 0.3 | 97.9 | 0.45 |

Note:
T represents time.

Preparation Example 8. Lyophilization of TGF-β
Receptor Fusion Protein Preparation TGF-β receptor fusion protein (fusion protein 9) prepa-
ration comprising a concentration of 50 mg/ml TGF-β
receptor fusion protein (fusion protein 9), 80 mg/ml sucrose,
and 0.4 mg/ml polysorbate 80 was prepared with a pH 6.2
buffer comprising 10 mM citric acid-sodium citrate. The
antibody was added at 6.3 mL/vial into a 20 mL vial, and
placed into a deep freezer for freeze-drying.

The lyophilization procedures includes pre-freezing, pri-
mary drying and secondary drying. Once the lyophilization
process was over, the vial was stoppered under vacuum. The
samples were reconstituted and a comparison was made
between before and after freeze-drying. The results show
that the reconstituted solution can maintain a favorable
performance as that of the solution preparation.

TABLE 18

| lyophilization steps of the preparations | | |
|---|---|---|
| Parameters of lyophilization | Temperature setting (° C.) | degree of vacuum (mBar) |
| pre-freezing | 5 | N/A |
| | −45 | N/A |

TABLE 18-continued

| lyophilization steps of the preparations | | |
|---|---|---|
| Parameters of lyophilization | Temperature setting (° C.) | degree of vacuum (mBar) |
| primary drying | −27 | 0.1 |
| secondary drying | 25 | 0.1 |
| | 25 | 0.01 |

Preparation Example 9. Other Optional Preparation
Compositions

In addition, the present disclosure also provides other
preparations of TGF-β receptor fusion protein (fusion pro-
tein 9) pharmaceutical preparations:

(1) 70 mg/ml fusion protein 9, 75 mg/ml sucrose, 0.4
mg/ml polysorbate 80, and 20 mM citric acid-sodium
citrate buffer, the final pH is 6.4;

(2) 80 mg/ml fusion protein 9, 85 mg/ml sucrose, 0.5
mg/ml polysorbate 80, and 15 mM citric acid-sodium
citrate buffer, the final pH is 6.2;

(3) 60 mg/ml fusion protein 9, 90 mg/ml sucrose, 0.6
mg/ml polysorbate 80, and 5 mM citric acid-sodium
citrate buffer, the final pH is 6.2;

(4) 30 mg/ml fusion protein 9, 60 mg/ml sucrose, 0.3
mg/ml polysorbate 80, and 30 mM citric acid-sodium
citrate buffer, the final pH is 6.3;

(5) 90 mg/ml fusion protein 9, 95 mg/ml sucrose, 0.2
mg/ml polysorbate 80, and 10 mM citric acid-sodium
citrate buffer, the final pH is 6.0;

(6) 100 mg/ml fusion protein 9, 70 mg/ml sucrose, 0.1
mg/ml polysorbate 80, and 25 mM citric acid-sodium
citrate buffer, the final pH is 6.5;

(7) 50 mg/ml fusion protein 9, 80 mg/ml sucrose, 0.4
mg/ml polysorbate 80, and 10 mM citric acid-sodium
citrate buffer, the final pH is 7.0;

(8) 50 mg/ml fusion protein 9, 80 mg/ml sucrose, 0.4
mg/ml polysorbate 80, and 10 mM citric acid-sodium
citrate buffer, the final pH is 7.5;

(9) 50 mg/ml fusion protein 9, 80 mg/ml sucrose, 0.4
mg/ml polysorbate 80, and 10 mM citric acid-sodium
citrate buffer, the final pH is 5.0;

(10) 60 mg/ml fusion protein 9, 70 mg/ml sucrose, 0.5
mg/ml polysorbate 80, and 15 mM citric acid-sodium
citrate buffer, the final pH is 5.5;

(11) 40 mg/ml fusion protein 9, 80 mg/ml sucrose, 0.5 mg/ml polysorbate 80, and 10 mM citric acid-sodium citrate buffer, the final pH is 6.2;

(12) 55 mg/ml fusion protein 9, 75 mg/ml sucrose, 0.3 mg/ml polysorbate 80, and 5 mM citric acid-sodium citrate buffer, the final pH is 6.0;

(13) 65 mg/ml fusion protein 9, 90 mg/ml sucrose, 0.7 mg/ml polysorbate 80, and 30 mM citric acid-sodium citrate buffer, the final pH is 7.5;

(14) 70 mg/ml fusion protein 9, 75 mg/ml sucrose, 0.8 mg/ml polysorbate 80, and 30 mM citric acid-sodium citrate buffer, the final pH is 7.0;

(15) 50 mg/ml fusion protein 9, 80 mg/ml sucrose, 0.8 mg/ml polysorbate 80, and 10 mM citric acid-sodium citrate buffer, the final pH is 7.0.

---

What is claimed is:

1. A pharmaceutical composition comprising:
about 0.5 mg/ml to about 100 mg/ml of a TGF-β receptor fusion protein;
about 5 mM to about 20 mM of a citric acid-sodium citrate buffer;
about 60 mg/ml to about 90 mg/ml of sucrose; and
about 0.4 mg/ml to about 0.8 mg/ml of polysorbate 80;
wherein the pH of the pharmaceutical composition is about 6.0 to about 6.5; and
wherein the TGF-β receptor fusion protein consists of:
a fusion peptide formed by a heavy chain of a PD-L1 antibody and TGF-βRII extracellular domain (TGF-βRII ECD), the sequence of which is set forth in SEQ ID NO: 23 or has at least 85% identity to the sequence set forth in SEQ ID NO: 23, and
a light chain of the PD-L1 antibody, the sequence of which is set forth in SEQ ID NO: 13 or has at least 85% identity to the sequence set forth in SEQ ID NO: 13.

2. The pharmaceutical composition according to claim 1, wherein the concentration of the citric acid-sodium citrate buffer is about 10 mM.

3. The pharmaceutical composition according to claim 1, wherein the concentration of the TGF-β receptor fusion protein is about 30 mg/ml to about 70 mg/ml.

4. The pharmaceutical composition according to claim 1, wherein the pH of the pharmaceutical composition is about 6.2.

5. The pharmaceutical composition according to claim 1, wherein the concentration of the sucrose is about 80 mg/ml.

6. The pharmaceutical composition according to claim 1, wherein the concentration of the polysorbate 80 is about 0.4 mg/ml.

7. The pharmaceutical composition according to claim 1, wherein the pharmaceutical composition comprises:
about 30 mg/ml to about 70 mg/ml of the TGF-β receptor fusion protein,
about 5 mM to about 20 mM of the citric acid-sodium citrate buffer,
about 60 mg/ml to about 90 mg/ml of sucrose, and
about 0.4 mg/ml to about 0.8 mg/ml of polysorbate 80;
and the pH of the pharmaceutical composition is about 6.0 to about 6.5.

8. The pharmaceutical composition according to claim 1, wherein the concentration of the TGF-β receptor fusion protein is about 50 mg/ml.

9. The pharmaceutical composition according to claim 1, wherein the pharmaceutical composition comprises:
about 50 mg/ml of the TGF-β receptor fusion protein,
about 10 mM of the citric acid-sodium citrate buffer,
about 80 mg/ml of sucrose, and
about 0.4 mg/ml of polysorbate 80; and
wherein the pH of the pharmaceutical composition is about 6.2.

10. A lyophilized preparation comprising a TGF-β receptor fusion protein, which is obtained by lyophilizing the pharmaceutical composition according to claim 1.

11. A reconstituted solution comprising a TGF-β receptor fusion protein, which is obtained by reconstituting the lyophilized preparation of claim 10.

12. A lyophilized preparation comprising a TGF-β receptor fusion protein, which can be reconstituted to form the pharmaceutical composition according to claim 1.

13. An article of manufacture, comprising one or more container(s), the one or more container comprising: the pharmaceutical composition according to claim 1.

14. A method for preparing the pharmaceutical composition of claim 1, the method comprises: a step of contacting the TGF-β receptor fusion protein with the buffer.

* * * * *

SEQUENCE LISTING

<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<221> NAME/KEY: DOMAIN
<223> OTHER INFORMATION: HCDR1

<400> SEQUENCE: 1

Ser Tyr Trp Met His
1               5

<210> SEQ ID NO 2
<211> LENGTH: 17
<212> TYPE: PRT
<213> ORGANISM: Artificial Sequence
<220> FEATURE:
<221> NAME/KEY: DOMAIN
<223> OTHER INFORMATION: HCDR2
<220> FEATURE:
<221> NAME/KEY: DOMAIN
<222> LOCATION: (3)..(3)
<223> OTHER INFORMATION: Xaa is selected from His or Gly
<220> FEATURE:
<221> NAME/KEY: DOMAIN
<222> LOCATION: (8)..(8)
<223> OTHER INFORMATION: Xaa is selected from Gly or Phe

<400> SEQUENCE: 2

Arg Ile Xaa Pro Asn Ser Gly Xaa Thr Ser Tyr Asn Glu Lys Phe Lys
1               5                   10                  15

Asn

<210> SEQ ID NO 3
<211> LENGTH: 10
<212> TYPE: PRT
<213> ORGANISM: Artificial Sequence
<220> FEATURE:
<221> NAME/KEY: DOMAIN
<223> OTHER INFORMATION: HCDR3

<400> SEQUENCE: 3

Gly Gly Ser Ser Tyr Asp Tyr Phe Asp Tyr
1               5                   10

<210> SEQ ID NO 4
<211> LENGTH: 15
<212> TYPE: PRT
<213> ORGANISM: Artificial Sequence
<220> FEATURE:
<221> NAME/KEY: DOMAIN
<223> OTHER INFORMATION: LCDR1

<400> SEQUENCE: 4

Arg Ala Ser Glu Ser Val Ser Ile His Gly Thr His Leu Met His
1               5                   10                  15

```
<210> SEQ ID NO 5
<211> LENGTH: 7
<212> TYPE: PRT
<213> ORGANISM: Artificial Sequence
<220> FEATURE:
<221> NAME/KEY: DOMAIN
<223> OTHER INFORMATION: LCDR2

<400> SEQUENCE: 5

Ala Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<221> NAME/KEY: DOMAIN
<223> OTHER INFORMATION: LCDR3

<400> SEQUENCE: 6

Gln Gln Ser Phe Glu Asp Pro Leu Thr
1               5

<210> SEQ ID NO 7
<211> LENGTH: 119
<212> TYPE: PRT
<213> ORGANISM: Artificial Sequence
<220> FEATURE:
<221> NAME/KEY: DOMAIN
<223> OTHER INFORMATION: Humanized PD-L1 antibody heavy chain variable
      region
<220> FEATURE:
<221> NAME/KEY: DOMAIN
<222> LOCATION: (52)..(52)
<223> OTHER INFORMATION: Xaa is selected from His or Gly
<220> FEATURE:
<221> NAME/KEY: DOMAIN
<222> LOCATION: (57)..(57)
<223> OTHER INFORMATION: Xaa is selected from Gly or Phe

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Xaa Pro Asn Ser Gly Xaa Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 8
<211> LENGTH: 111
<212> TYPE: PRT
<213> ORGANISM: Artificial Sequence
<220> FEATURE:
```

<221> NAME/KEY: DOMAIN
<223> OTHER INFORMATION: Humanized PD-L1 antibody light chain variable
      region

<400> SEQUENCE: 8

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 9
<211> LENGTH: 119
<212> TYPE: PRT
<213> ORGANISM: Artificial Sequence
<220> FEATURE:
<221> NAME/KEY: DOMAIN
<223> OTHER INFORMATION: PD-L1 antibody heavy chain variable region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 10
<211> LENGTH: 17
<212> TYPE: PRT
<213> ORGANISM: Artificial Sequence
<220> FEATURE:
<221> NAME/KEY: DOMAIN
<223> OTHER INFORMATION: HCDR2

<400> SEQUENCE: 10

Arg Ile Gly Pro Asn Ser Gly Phe Thr Ser Tyr Asn Glu Lys Phe Lys
1               5                   10                  15

Asn

-continued

<210> SEQ ID NO 11
<211> LENGTH: 111
<212> TYPE: PRT
<213> ORGANISM: Artificial Sequence
<220> FEATURE:
<221> NAME/KEY: DOMAIN
<223> OTHER INFORMATION: PD-L1 antibody light chain variable region

<400> SEQUENCE: 11

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 12
<211> LENGTH: 446
<212> TYPE: PRT
<213> ORGANISM: Artificial Sequence
<220> FEATURE:
<221> NAME/KEY: CHAIN
<223> OTHER INFORMATION: PD-L1 antibody heavy chain sequence: Ig G4(AA)
      (S228P)

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

-continued

```
Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Ala Ala Gly Gly Pro Ser Val Phe
225                         230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Ala
        435                 440                 445
```

<210> SEQ ID NO 13
<211> LENGTH: 218
<212> TYPE: PRT
<213> ORGANISM: Artificial Sequence
<220> FEATURE:
<221> NAME/KEY: CHAIN
<223> OTHER INFORMATION: PD-L1 antibody light chain sequence

<400> SEQUENCE: 13

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys Arg
            100                 105                 110
```

-continued

```
Thr Val Ala Ala Pro Ser Val Phe Ile Phe Pro Pro Ser Asp Glu Gln
    115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
    210                 215
```

```
<210> SEQ ID NO 14
<211> LENGTH: 136
<212> TYPE: PRT
<213> ORGANISM: Artificial Sequence
<220> FEATURE:
<221> NAME/KEY: PEPTIDE
<223> OTHER INFORMATION: TGF-beta RII ECD sequence: ECD (1-136)

<400> SEQUENCE: 14

Ile Pro Pro His Val Gln Lys Ser Val Asn Asn Asp Met Ile Val Thr
1                 5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
                100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135
```

```
<210> SEQ ID NO 15
<211> LENGTH: 117
<212> TYPE: PRT
<213> ORGANISM: Artificial Sequence
<220> FEATURE:
<221> NAME/KEY: PEPTIDE
<223> OTHER INFORMATION: TGF-beta RII ECD sequence with a truncation or
      absence of 19 aa at N-terminus: ECD (20-136)

<400> SEQUENCE: 15

Gly Ala Val Lys Phe Pro Gln Leu Cys Lys Phe Cys Asp Val Arg Phe
1                 5                   10                  15

Ser Thr Cys Asp Asn Gln Lys Ser Cys Met Ser Asn Cys Ser Ile Thr
                20                  25                  30

Ser Ile Cys Glu Lys Pro Gln Glu Val Cys Val Ala Val Trp Arg Lys
```

```
        35              40              45

Asn Asp Glu Asn Ile Thr Leu Glu Thr Val Cys His Asp Pro Lys Leu
   50              55              60

Pro Tyr His Asp Phe Ile Leu Glu Asp Ala Ala Ser Pro Lys Cys Ile
65              70              75              80

Met Lys Glu Lys Lys Pro Gly Glu Thr Phe Phe Met Cys Ser Cys
           85              90              95

Ser Ser Asp Glu Cys Asn Asp Asn Ile Ile Phe Ser Glu Glu Tyr Asn
           100             105             110

Thr Ser Asn Pro Asp
        115
```

```
<210> SEQ ID NO 16
<211> LENGTH: 115
<212> TYPE: PRT
<213> ORGANISM: Artificial Sequence
<220> FEATURE:
<221> NAME/KEY: PEPTIDE
<223> OTHER INFORMATION: TGF-beta RII ECD sequence with a truncation or
      absence of 21 aa at N-terminus: ECD (22-136)

<400> SEQUENCE: 16

Val Lys Phe Pro Gln Leu Cys Lys Phe Cys Asp Val Arg Phe Ser Thr
1               5               10              15

Cys Asp Asn Gln Lys Ser Cys Met Ser Asn Cys Ser Ile Thr Ser Ile
           20              25              30

Cys Glu Lys Pro Gln Glu Val Cys Val Ala Val Trp Arg Lys Asn Asp
        35              40              45

Glu Asn Ile Thr Leu Glu Thr Val Cys His Asp Pro Lys Leu Pro Tyr
   50              55              60

His Asp Phe Ile Leu Glu Asp Ala Ala Ser Pro Lys Cys Ile Met Lys
65              70              75              80

Glu Lys Lys Lys Pro Gly Glu Thr Phe Phe Met Cys Ser Cys Ser Ser
           85              90              95

Asp Glu Cys Asn Asp Asn Ile Ile Phe Ser Glu Glu Tyr Asn Thr Ser
           100             105             110

Asn Pro Asp
        115
```

```
<210> SEQ ID NO 17
<211> LENGTH: 122
<212> TYPE: PRT
<213> ORGANISM: Artificial Sequence
<220> FEATURE:
<221> NAME/KEY: PEPTIDE
<223> OTHER INFORMATION: TGF-beta RII ECD sequence with a truncation or
      absence of 14 aa at N-terminus: ECD (15-136)

<400> SEQUENCE: 17

Val Thr Asp Asn Asn Gly Ala Val Lys Phe Pro Gln Leu Cys Lys Phe
1               5               10              15

Cys Asp Val Arg Phe Ser Thr Cys Asp Asn Gln Lys Ser Cys Met Ser
           20              25              30

Asn Cys Ser Ile Thr Ser Ile Cys Glu Lys Pro Gln Glu Val Cys Val
        35              40              45

Ala Val Trp Arg Lys Asn Asp Glu Asn Ile Thr Leu Glu Thr Val Cys
   50              55              60

His Asp Pro Lys Leu Pro Tyr His Asp Phe Ile Leu Glu Asp Ala Ala
65              70              75              80
```

-continued

```
Ser Pro Lys Cys Ile Met Lys Glu Lys Lys Pro Gly Glu Thr Phe
                85              90              95

Phe Met Cys Ser Cys Ser Ser Asp Glu Cys Asn Asp Asn Ile Ile Phe
            100             105             110

Ser Glu Glu Tyr Asn Thr Ser Asn Pro Asp
        115             120
```

```
<210> SEQ ID NO 18
<211> LENGTH: 236
<212> TYPE: PRT
<213> ORGANISM: Artificial Sequence
<220> FEATURE:
<221> NAME/KEY: PEPTIDE
<223> OTHER INFORMATION: Antigen used for detection: PD-L1-His

<400> SEQUENCE: 18

Phe Thr Val Thr Val Pro Lys Asp Leu Tyr Val Val Glu Tyr Gly Ser
1               5               10              15

Asn Met Thr Ile Glu Cys Lys Phe Pro Val Glu Lys Gln Leu Asp Leu
            20              25              30

Ala Ala Leu Ile Val Tyr Trp Glu Met Glu Asp Lys Asn Ile Ile Gln
        35              40              45

Phe Val His Gly Glu Glu Asp Leu Lys Val Gln His Ser Ser Tyr Arg
    50              55              60

Gln Arg Ala Arg Leu Leu Lys Asp Gln Leu Ser Leu Gly Asn Ala Ala
65              70              75              80

Leu Gln Ile Thr Asp Val Lys Leu Gln Asp Ala Gly Val Tyr Arg Cys
                85              90              95

Met Ile Ser Tyr Gly Gly Ala Asp Tyr Lys Arg Ile Thr Val Lys Val
            100             105             110

Asn Ala Pro Tyr Asn Lys Ile Asn Gln Arg Ile Leu Val Val Asp Pro
        115             120             125

Val Thr Ser Glu His Glu Leu Thr Cys Gln Ala Glu Gly Tyr Pro Lys
        130             135             140

Ala Glu Val Ile Trp Thr Ser Ser Asp His Gln Val Leu Ser Gly Lys
145             150             155             160

Thr Thr Thr Thr Asn Ser Lys Arg Glu Glu Lys Leu Phe Asn Val Thr
            165             170             175

Ser Thr Leu Arg Ile Asn Thr Thr Thr Asn Glu Ile Phe Tyr Cys Thr
            180             185             190

Phe Arg Arg Leu Asp Pro Glu Glu Asn His Thr Ala Glu Leu Val Ile
            195             200             205

Pro Glu Leu Pro Leu Ala His Pro Pro Asn Glu Arg Glu Gln Lys Leu
        210             215             220

Ile Ser Glu Glu Asp Leu His His His His His His
225             230             235
```

```
<210> SEQ ID NO 19
<211> LENGTH: 346
<212> TYPE: PRT
<213> ORGANISM: Artificial Sequence
<220> FEATURE:
<221> NAME/KEY: PEPTIDE
<223> OTHER INFORMATION: Control 1 (20T-Fc): ECD(20-136)-Fc, a fusion
      protein of truncated TGF-beta RII ECD fragment ECD (20-136) and Fc

<400> SEQUENCE: 19

Gly Ala Val Lys Phe Pro Gln Leu Cys Lys Phe Cys Asp Val Arg Phe
```

```
1               5              10              15
Ser Thr Cys Asp Asn Gln Lys Ser Cys Met Ser Asn Cys Ser Ile Thr
            20              25              30

Ser Ile Cys Glu Lys Pro Gln Glu Val Cys Val Ala Val Trp Arg Lys
            35              40              45

Asn Asp Glu Asn Ile Thr Leu Glu Thr Val Cys His Asp Pro Lys Leu
    50              55              60

Pro Tyr His Asp Phe Ile Leu Glu Asp Ala Ala Ser Pro Lys Cys Ile
65              70              75              80

Met Lys Glu Lys Lys Lys Pro Gly Glu Thr Phe Phe Met Cys Ser Cys
                85              90              95

Ser Ser Asp Glu Cys Asn Asp Asn Ile Ile Phe Ser Glu Glu Tyr Asn
            100             105             110

Thr Ser Asn Pro Asp Ala Glu Ser Lys Tyr Gly Pro Pro Cys Pro Pro
            115             120             125

Cys Pro Ala Pro Glu Ala Ala Gly Gly Pro Ser Val Phe Leu Phe Pro
    130             135             140

Pro Lys Pro Lys Asp Thr Leu Met Ile Ser Arg Thr Pro Glu Val Thr
145             150             155             160

Cys Val Val Val Asp Val Ser Gln Glu Asp Pro Glu Val Gln Phe Asn
            165             170             175

Trp Tyr Val Asp Gly Val Glu Val His Asn Ala Lys Thr Lys Pro Arg
            180             185             190

Glu Glu Gln Phe Asn Ser Thr Tyr Arg Val Val Ser Val Leu Thr Val
            195             200             205

Leu His Gln Asp Trp Leu Asn Gly Lys Glu Tyr Lys Cys Lys Val Ser
    210             215             220

Asn Lys Gly Leu Pro Ser Ser Ile Glu Lys Thr Ile Ser Lys Ala Lys
225             230             235             240

Gly Gln Pro Arg Glu Pro Gln Val Tyr Thr Leu Pro Pro Ser Gln Glu
            245             250             255

Glu Met Thr Lys Asn Gln Val Ser Leu Thr Cys Leu Val Lys Gly Phe
            260             265             270

Tyr Pro Ser Asp Ile Ala Val Glu Trp Glu Ser Asn Gly Gln Pro Glu
            275             280             285

Asn Asn Tyr Lys Thr Thr Pro Pro Val Leu Asp Ser Asp Gly Ser Phe
    290             295             300

Phe Leu Tyr Ser Arg Leu Thr Val Asp Lys Ser Arg Trp Gln Glu Gly
305             310             315             320

Asn Val Phe Ser Cys Ser Val Met His Glu Ala Leu His Asn His Tyr
            325             330             335

Thr Gln Lys Ser Leu Ser Leu Ser Leu Gly
            340             345
```

<210> SEQ ID NO 20
<211> LENGTH: 344
<212> TYPE: PRT
<213> ORGANISM: Artificial Sequence
<220> FEATURE:
<221> NAME/KEY: PEPTIDE
<223> OTHER INFORMATION: Control 2 (22T-Fc): ECD(22-136)-Fc, a fusion
      protein of truncated TGF-beta RII ECD fragment ECD (22-136) and Fc

<400> SEQUENCE: 20

```
Val Lys Phe Pro Gln Leu Cys Lys Phe Cys Asp Val Arg Phe Ser Thr
1               5              10              15
```

-continued

```
Cys Asp Asn Gln Lys Ser Cys Met Ser Asn Cys Ser Ile Thr Ser Ile
        20              25              30

Cys Glu Lys Pro Gln Glu Val Cys Val Ala Val Trp Arg Lys Asn Asp
        35              40              45

Glu Asn Ile Thr Leu Glu Thr Val Cys His Asp Pro Lys Leu Pro Tyr
    50              55              60

His Asp Phe Ile Leu Glu Asp Ala Ala Ser Pro Lys Cys Ile Met Lys
65              70              75              80

Glu Lys Lys Lys Pro Gly Glu Thr Phe Phe Met Cys Ser Cys Ser Ser
            85              90              95

Asp Glu Cys Asn Asp Asn Ile Ile Phe Ser Glu Glu Tyr Asn Thr Ser
        100             105             110

Asn Pro Asp Ala Glu Ser Lys Tyr Gly Pro Pro Cys Pro Pro Cys Pro
        115             120             125

Ala Pro Glu Ala Ala Gly Gly Pro Ser Val Phe Leu Phe Pro Pro Lys
        130             135             140

Pro Lys Asp Thr Leu Met Ile Ser Arg Thr Pro Glu Val Thr Cys Val
145             150             155             160

Val Val Asp Val Ser Gln Glu Asp Pro Glu Val Gln Phe Asn Trp Tyr
            165             170             175

Val Asp Gly Val Glu Val His Asn Ala Lys Thr Lys Pro Arg Glu Glu
            180             185             190

Gln Phe Asn Ser Thr Tyr Arg Val Val Ser Val Leu Thr Val Leu His
        195             200             205

Gln Asp Trp Leu Asn Gly Lys Glu Tyr Lys Cys Lys Val Ser Asn Lys
        210             215             220

Gly Leu Pro Ser Ser Ile Glu Lys Thr Ile Ser Lys Ala Lys Gly Gln
225             230             235             240

Pro Arg Glu Pro Gln Val Tyr Thr Leu Pro Pro Ser Gln Glu Glu Met
            245             250             255

Thr Lys Asn Gln Val Ser Leu Thr Cys Leu Val Lys Gly Phe Tyr Pro
        260             265             270

Ser Asp Ile Ala Val Glu Trp Glu Ser Asn Gly Gln Pro Glu Asn Asn
        275             280             285

Tyr Lys Thr Thr Pro Pro Val Leu Asp Ser Asp Gly Ser Phe Phe Leu
        290             295             300

Tyr Ser Arg Leu Thr Val Asp Lys Ser Arg Trp Gln Glu Gly Asn Val
305             310             315             320

Phe Ser Cys Ser Val Met His Glu Ala Leu His Asn His Tyr Thr Gln
            325             330             335

Lys Ser Leu Ser Leu Ser Leu Gly
        340
```

<210> SEQ ID NO 21
<211> LENGTH: 216
<212> TYPE: PRT
<213> ORGANISM: Artificial Sequence
<220> FEATURE:
<221> NAME/KEY: CHAIN
<223> OTHER INFORMATION: In FP17022 fusion protein, the amino acid
      sequence of PD-L1 antibody 2 light chain

<400> SEQUENCE: 21

```
Gln Ser Ala Leu Thr Gln Pro Ala Ser Val Ser Gly Ser Pro Gly Gln
1               5               10              15
```

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215
```

```
<210> SEQ ID NO 22
<211> LENGTH: 607
<212> TYPE: PRT
<213> ORGANISM: Artificial Sequence
<220> FEATURE:
<221> NAME/KEY: PEPTIDE
<223> OTHER INFORMATION: In FP17022 fusion protein, the fusion peptide
      sequence of PD-L1 antibody 2 heavy chain/TGF-beta RII ECD (1-136)

<400> SEQUENCE: 22
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
```

-continued

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Ala Gly Gly Gly Gly Ser Gly Gly Gly Gly Ser Gly Gly Gly Gly
        450                 455                 460

Ser Gly Gly Gly Gly Ser Gly Ile Pro Pro His Val Gln Lys Ser Val
465                 470                 475                 480

Asn Asn Asp Met Ile Val Thr Asp Asn Asn Gly Ala Val Lys Phe Pro
                485                 490                 495

Gln Leu Cys Lys Phe Cys Asp Val Arg Phe Ser Thr Cys Asp Asn Gln
                500                 505                 510

Lys Ser Cys Met Ser Asn Cys Ser Ile Thr Ser Ile Cys Glu Lys Pro
                515                 520                 525

Gln Glu Val Cys Val Ala Val Trp Arg Lys Asn Asp Glu Asn Ile Thr
        530                 535                 540

Leu Glu Thr Val Cys His Asp Pro Lys Leu Pro Tyr His Asp Phe Ile
545                 550                 555                 560

Leu Glu Asp Ala Ala Ser Pro Lys Cys Ile Met Lys Glu Lys Lys Lys
                565                 570                 575
```

-continued

```
Pro Gly Glu Thr Phe Phe Met Cys Ser Cys Ser Ser Asp Glu Cys Asn
        580                 585                 590

Asp Asn Ile Ile Phe Ser Glu Glu Tyr Asn Thr Ser Asn Pro Asp
        595                 600                 605
```

<210> SEQ ID NO 23
<211> LENGTH: 584
<212> TYPE: PRT
<213> ORGANISM: Artificial Sequence
<220> FEATURE:
<221> NAME/KEY: PEPTIDE
<223> OTHER INFORMATION: In fusion protein 9,the fusion peptide sequence
      of the fused PD-L1 antibody heavy chain-(G4S)4G-TGF-beta RII ECD
      (20-136)

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
        20                  25                  30

Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320
```

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Ala Gly Gly
            435                 440                 445

Gly Gly Ser Gly Gly Gly Gly Ser Gly Gly Gly Gly Ser Gly Gly Gly
            450                 455                 460

Gly Ser Gly Gly Ala Val Lys Phe Pro Gln Leu Cys Lys Phe Cys Asp
465                 470                 475                 480

Val Arg Phe Ser Thr Cys Asp Asn Gln Lys Ser Cys Met Ser Asn Cys
                485                 490                 495

Ser Ile Thr Ser Ile Cys Glu Lys Pro Gln Glu Val Cys Val Ala Val
            500                 505                 510

Trp Arg Lys Asn Asp Glu Asn Ile Thr Leu Glu Thr Val Cys His Asp
            515                 520                 525

Pro Lys Leu Pro Tyr His Asp Phe Ile Leu Glu Asp Ala Ala Ser Pro
            530                 535                 540

Lys Cys Ile Met Lys Glu Lys Lys Lys Pro Gly Glu Thr Phe Phe Met
545                 550                 555                 560

Cys Ser Cys Ser Ser Asp Glu Cys Asn Asp Asn Ile Ile Phe Ser Glu
                565                 570                 575

Glu Tyr Asn Thr Ser Asn Pro Asp
            580

<210> SEQ ID NO 24
<211> LENGTH: 587
<212> TYPE: PRT
<213> ORGANISM: Artificial Sequence
<220> FEATURE:
<221> NAME/KEY: PEPTIDE
<223> OTHER INFORMATION: In fusion protein 15, the fusion peptide
      sequence of the fused PD-L1 antibody heavy chain-(G4S)5G-TGF
      -beta RII ECD (22-136)

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Arg Ile Gly Pro Asn Ser Gly Phe Thr Ser Tyr Asn Glu Lys Phe
        50                  55                  60

Lys Asn Arg Val Thr Met Thr Arg Asp Thr Ser Thr Ser Thr Val Tyr
65                  70                  75                  80

-continued

```
Met Glu Leu Ser Ser Leu Arg Ser Glu Asp Thr Ala Val Tyr Tyr Cys
            85              90              95

Ala Arg Gly Gly Ser Ser Tyr Asp Tyr Phe Asp Tyr Trp Gly Gln Gly
            100             105             110

Thr Thr Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Lys Thr Tyr Thr Cys Asn Val Asp His Lys Pro
            195             200             205

Ser Asn Thr Lys Val Asp Lys Arg Val Glu Ser Lys Tyr Gly Pro Pro
    210             215             220

Cys Pro Pro Cys Pro Ala Pro Glu Ala Ala Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser Gln Glu Asp Pro Glu Val
            260             265             270

Gln Phe Asn Trp Tyr Val Asp Gly Val Glu Val His Asn Ala Lys Thr
            275             280             285

Lys Pro Arg Glu Glu Gln Phe Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Gly Leu Pro Ser Ser Ile Glu Lys Thr Ile Ser
            325             330             335

Lys Ala Lys Gly Gln Pro Arg Glu Pro Gln Val Tyr Thr Leu Pro Pro
            340             345             350

Ser Gln Glu Glu Met Thr Lys Asn Gln Val Ser Leu Thr Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Arg Leu Thr Val Asp Lys Ser Arg Trp
            405             410             415

Gln Glu Gly Asn Val Phe Ser Cys Ser Val Met His Glu Ala Leu His
            420             425             430

Asn His Tyr Thr Gln Lys Ser Leu Ser Leu Ser Leu Gly Ala Gly Gly
            435             440             445

Gly Gly Ser Gly Gly Gly Gly Ser Gly Gly Gly Gly Ser Gly Gly Gly
    450             455             460

Gly Ser Gly Gly Gly Gly Ser Gly Val Lys Phe Pro Gln Leu Cys Lys
465             470             475             480

Phe Cys Asp Val Arg Phe Ser Thr Cys Asp Asn Gln Lys Ser Cys Met
            485             490             495
```

```
Ser Asn Cys Ser Ile Thr Ser Ile Cys Glu Lys Pro Gln Glu Val Cys
        500                 505                 510

Val Ala Val Trp Arg Lys Asn Asp Glu Asn Ile Thr Leu Glu Thr Val
        515                 520                 525

Cys His Asp Pro Lys Leu Pro Tyr His Asp Phe Ile Leu Glu Asp Ala
        530                 535                 540

Ala Ser Pro Lys Cys Ile Met Lys Glu Lys Lys Lys Pro Gly Glu Thr
545                 550                 555                 560

Phe Phe Met Cys Ser Cys Ser Ser Asp Glu Cys Asn Asp Asn Ile Ile
                565                 570                 575

Phe Ser Glu Glu Tyr Asn Thr Ser Asn Pro Asp
            580                 585
```

```
<210> SEQ ID NO 25
<211> LENGTH: 16
<212> TYPE: PRT
<213> ORGANISM: Artificial Sequence
<220> FEATURE:
<221> NAME/KEY: PEPTIDE
<222> LOCATION: (1)..(16)
<223> OTHER INFORMATION: linker

<400> SEQUENCE: 25

Gly Gly Gly Gly Ser Gly Gly Gly Gly Ser Gly Gly Gly Gly Ser Gly
1               5                   10                  15
```

```
<210> SEQ ID NO 26
<211> LENGTH: 21
<212> TYPE: PRT
<213> ORGANISM: Artificial Sequence
<220> FEATURE:
<221> NAME/KEY: PEPTIDE
<222> LOCATION: (1)..(21)
<223> OTHER INFORMATION: linker

<400> SEQUENCE: 26

Gly Gly Gly Gly Ser Gly Gly Gly Gly Ser Gly Gly Gly Gly Ser Gly
1               5                   10                  15

Gly Gly Gly Ser Gly
            20
```

```
<210> SEQ ID NO 27
<211> LENGTH: 26
<212> TYPE: PRT
<213> ORGANISM: Artificial Sequence
<220> FEATURE:
<221> NAME/KEY: PEPTIDE
<222> LOCATION: (1)..(26)
<223> OTHER INFORMATION: linker

<400> SEQUENCE: 27

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly
            20                  25
```

```
<210> SEQ ID NO 28
<211> LENGTH: 31
<212> TYPE: PRT
<213> ORGANISM: Artificial Sequence
<220> FEATURE:
<221> NAME/KEY: PEPTIDE
<222> LOCATION: (1)..(31)
<223> OTHER INFORMATION: linker
```

-continued

```
<400> SEQUENCE: 28

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly
            20                  25                  30
```